(12) United States Patent
Lee et al.

(10) Patent No.: US 10,993,883 B2
(45) Date of Patent: May 4, 2021

(54) SYSTEMS AND METHODS FOR PROMOTING MEDICATION ADHERENCE

(71) Applicant: Agape Assets, LLC, Pinole, CA (US)

(72) Inventors: Scott E. Lee, Pinole, CA (US); Carl Wong, Cerritos, CA (US); Albert Alaan, Redondo Beach, CA (US); Taiki Nishihara, Berkeley, CA (US)

(73) Assignee: Agape Assets, LLC, Pinole, CA (US)

( * ) Notice: Subject to any disclaimer, the term of this patent is extended or adjusted under 35 U.S.C. 154(b) by 0 days.

(21) Appl. No.: 16/750,452

(22) Filed: Jan. 23, 2020

(65) Prior Publication Data

US 2020/0155415 A1 May 21, 2020

Related U.S. Application Data

(63) Continuation-in-part of application No. 15/807,809, filed on Nov. 9, 2017, now abandoned.

(60) Provisional application No. 62/419,606, filed on Nov. 9, 2016.

(51) Int. Cl.
*A61J 7/04* (2006.01)
*A61F 9/00* (2006.01)

(52) U.S. Cl.
CPC ............ *A61J 7/0427* (2015.05); *A61F 9/0008* (2013.01); *A61J 7/0418* (2015.05); *A61J 7/0481* (2013.01); *A61J 2200/30* (2013.01)

(58) Field of Classification Search
CPC ...... A61J 7/0418; A61J 7/0427; A61J 7/0481; A61J 2200/30; G07F 17/0092; G16H 20/13

USPC .................................................. 700/231–244
See application file for complete search history.

(56) References Cited

U.S. PATENT DOCUMENTS

| | | | | |
|---|---|---|---|---|
| 5,625,334 A | * | 4/1997 | Compton | A61J 7/0472 116/308 |
| 6,335,692 B1 | * | 1/2002 | Compton | A61J 7/0472 340/309.4 |
| 9,785,750 B2 | * | 10/2017 | Coe | A61J 7/0084 |
| 2018/0028410 A1 | * | 2/2018 | Yun | A61J 7/0481 |
| 2018/0126273 A1 | * | 5/2018 | Lee | A61J 7/0418 |
| 2018/0168935 A1 | * | 6/2018 | Chen | A61J 7/0436 |

* cited by examiner

*Primary Examiner* — Timothy R Waggoner
(74) *Attorney, Agent, or Firm* — PatentFile, LLC; Bradley C. Fach; Steven R. Kick

(57) ABSTRACT

A system for promoting medication adherence is provided. The system may receive medical information and medication access information via a medication adherence device, the medication adherence device having a housing configured to be removably coupled to a medicine container. The information may be used to form one or more blind spots which representative of symptoms of glaucoma and which may be produced on the display screen of a patient's client device. The system may use Gamblification and/or Gamification in which a blind spot obscures portions of a game of chance program and/or novelty game type program, respectively, from being observed on the display screen. As medical information and medication compliance information is received, the number, size, opacity, and/or shape of the blind spots produced on the display screen of a patient's client device may change to provide actual perception of visual loss which spurs patients to compliance.

10 Claims, 18 Drawing Sheets

SYSTEMS AND METHODS FOR PROMOTING MEDICATION ADHERENCE

CROSS REFERENCE TO RELATED APPLICATIONS

This application is a continuation-in-part of U.S. Non-Provisional application Ser. No. 15/807,809, filed on Nov. 9, 2017, entitled "SYSTEMS AND METHODS FOR PROMOTING MEDICATION ADHERENCE", which claims the benefit of U.S. Provisional Patent Application Ser. No. 62/419,606, filed on Nov. 9, 2016, entitled "SYSTEMS AND METHODS FOR PROMOTING MEDICATION ADHERENCE", the entire disclosures of which are incorporated by reference herein.

FIELD OF THE INVENTION

This patent specification relates to the field of medication adherence. More specifically, this patent specification relates to systems and methods that are configured to increase patient compliance with medication and adherence to eye drop regimens.

BACKGROUND

Glaucoma is a highly prevalent cause of blindness worldwide. Glaucoma is an optic neuropathy, often associated with cupping of the optic nerve head, higher intraocular pressure, and visual field loss. Glaucoma is often an insidious disease and can be asymptomatic in patients for decades before causing serious vision loss. Glaucoma typically manifests in causing visual loss in the periphery. Patients are usually unaware of vision changes in their periphery due to the slow progression of the disease. Visual field testing is called perimetry and is essential in diagnosing glaucoma. Various patents have described testing of visual field on smartphones and tablets as a means of portable perimetry. Smartphone, tablet based portable perimetry are available in the market for testing. However, these programs or video games are a means to diagnosis to detect visual field loss. It is difficult enough to test a patient using a standard automated perimeter in the medical office, let alone in an uncontrolled environment, no matter how entertaining the visual stimuli may be. Testing peripheral vision does little to encourage medication regimen adherence without demonstrating vision loss to the patient.

Therefore, a need exists for new devices and systems to increase compliance with medication adherence for eye drop regimens. A further need exists for new devices and systems to inform patients of vision changes in their periphery due to disease progression. A need exists for new devices and systems which encourage medication regimen adherence by demonstrating vision loss to the patient. Finally, there is no currently available method of quantifying actual compliance of medication adherence, with respect to eye drops. Ophthalmologists are in need of this data to determine if poor treatment is due to compliance or simply the progression of the glaucoma.

BRIEF SUMMARY OF THE INVENTION

A system for promoting medication adherence to a user of a client device is provided. In some embodiments, the system may include one or more client devices in communication with one or more servers allowing for the communication of data between the client devices and servers. The users may include patients and vision care providers, each of which may have access to a client device. The system may receive medical information and medication compliance information of a patient which may be used to form one or more which may be produced on the display screen of a patient's client device in which the blind spots are representative of glaucoma associated scotomas. The blind spots may obscure or otherwise black out portions of the display screen of a patient's client device thereby decreasing the amount of text or graphical information visible to the patient. As medical information and medication compliance information is received, the number, size, opacity, and/or shape of the blind spots produced on the display screen of a patient's client device may change to provide actual perception of visual loss which spurs patients to compliance and a better understanding of their disease. The client device does not test visual changes or scotomas, but rather is an educational tool to demonstrate vision loss.

A method for promoting user medication adherence with a client device is provided. In some embodiments, the method may include the steps of: receiving intraocular pressure information of the user; receiving medication information describing directions on how the user is to use the medication; determining if the user is taking the medication as directed in the medical information; and producing a blind spot on the display of the client device that obscures information on the display of the client device and which increases in size and opacity when the user does not take the medication as directed.

In further embodiments, a method for promoting medication adherence to a user of a client device may include the step of reminding the user to take the medication as directed. The reminders may visually indicate: which medication to take; in which eye the medication is to be taken; and/or at what time the medication is to be taken preferably by showing pictures of the medication container, packaging, name, and/or dosage. Aside from the medication adherence device alert sounds, the reminders may also include voice messages, optionally provided by a patient's doctor, which may be used to form audio reminders.

In still further embodiments, the system may include a medication adherence device which may include a unibody housing configured to be removably coupled to a medicine container of a medicine that is prescribed to a patient or user. The medication adherence device may be configured to provide medication access information to the system which may be used to determine if a user has missed and/or performed one or more compliance events.

In further embodiments, the medication adherence device may include a unibody and a station. The unibody may include: a unibody housing configured to be removably coupled to a medicine container; an inertial measurement unit configured to record motion data describing the movement of the unibody, and therefore describing the movement of a medicine container that the unibody is coupled to; and a unibody data interface in communication with the inertial measurement unit. The station may include: a station data interface configured to receive motion data from the unibody data interface; and a station processing unit in communication with the station data interface, the station processing unit configured to generate medication access information using the motion data. Preferably, data and power may be communicated between the unibody and station when the unibody is positioned proximate to the station, such as by being positioned in a station cavity.

In still further embodiments, a computer-implemented method for promoting medication adherence by a user of a client device based on the medication adherence history of the user is provided. The method may include the steps of: receiving treatment plan information for the user, in which the treatment plan information comprises information describing a daily number of compliance events for a medication of the user; determining, via a computing device processor, if the user has missed a compliance event preferably using medication access information received from a medication adherence device; identifying, via a computing device processor, a cumulative number of missed compliance events for the medication of the user; and producing, via a computing device processor, a blind spot on the display screen of the client device, wherein the blind spot obscures information on a portion of the display screen, and wherein the blind spot increases in size and/or opacity in proportion to an increasing cumulative number of missed compliance events.

BRIEF DESCRIPTION OF THE DRAWINGS

Some embodiments of the present invention are illustrated as an example and are not limited by the figures of the accompanying drawings, in which like references may indicate similar elements and in which.

DETAILED DESCRIPTION OF THE INVENTION

Figure 1:
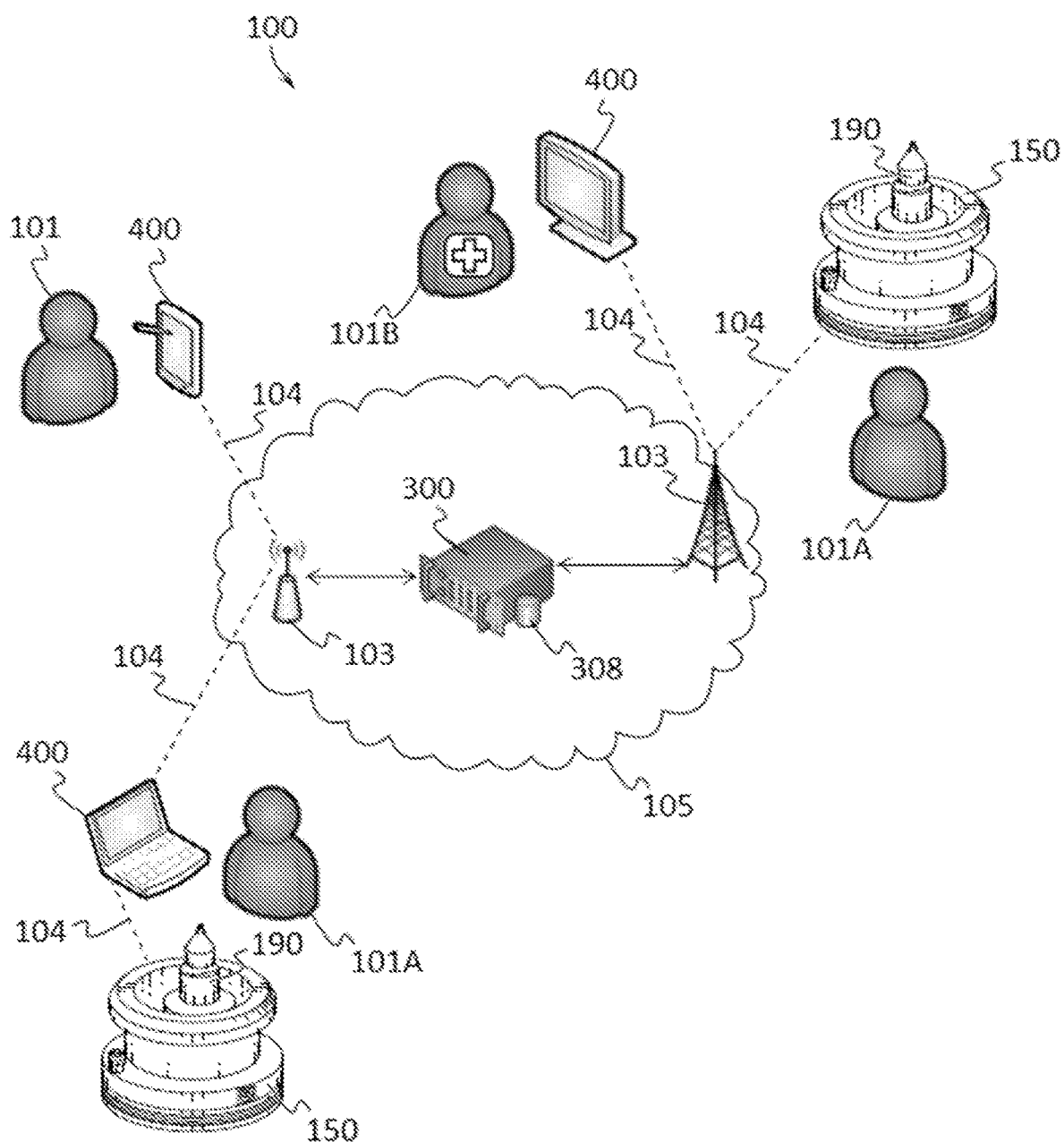
FIG. 1 depicts an illustrative example of some of the components and computer implemented methods which may be found in a system for promoting medication adherence according to various embodiments described herein.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

Definitions

As used herein, the term "computer" refers to a machine, apparatus, or device that is capable of accepting and performing logic operations from software code. The term "application", "software", "software code" or "computer software" refers to any set of instructions operable to cause a computer to perform an operation. Software code may be operated on by a "rules engine" or processor. Thus, the methods and systems of the present invention may be performed by a computer based on instructions received by computer software.

The term "electronic device" as used herein is a type of computer comprising circuitry and configured to generally perform functions such as recording audio, photos, and videos; displaying or reproducing audio, photos, and videos; storing, retrieving, or manipulation of electronic data; providing electrical communications and network connectivity; or any other similar function. Non-limiting examples of electronic devices include: personal computers (PCs), workstations, laptops, tablet PCs including the iPad, cell phones including iOS phones made by Apple Inc., Android OS phones, Microsoft OS phones, Blackberry phones, digital music players, or any electronic device capable of running computer software and displaying information to a user, memory cards, other memory storage devices, digital cameras, external battery packs, external charging devices, and the like. Certain types of electronic devices which are portable and easily carried by a person from one location to another may sometimes be referred to as a "portable electronic device" or "portable device". Some non-limiting examples of portable devices include: cell phones, smartphones, tablet computers, laptop computers, wearable computers such as Apple Watch, other smartwatches, Fitbit, other wearable fitness trackers, Google Glasses, and the like.

The term "client device" or sometimes "electronic device" as used herein is a type of computer generally operated by a person or user of the system. In some embodiments, a client device is a smartphone or computer configured to receive and transmit data to a server or other electronic device which may be operated locally or in the cloud. Non-limiting examples of client devices include: personal computers (PCs), workstations, laptops, tablet PCs including the iPad, cell phones including iOS phones made by Apple Inc., Android OS phones, Microsoft OS phones, Blackberry phones, or generally any electronic device capable of running computer software and displaying information to a user. Certain types of client devices which are portable and easily carried by a person from one location to another may sometimes be referred to as a "mobile device" or "portable device". Some non-limiting examples of mobile devices include: cell phones, smartphones, tablet computers, laptop computers, wearable computers such as Apple Watch, other smartwatches, Fitbit, other wearable fitness trackers, Google Glasses, and the like.

The term "computer readable medium" as used herein refers to any medium that participates in providing instructions to the processor for execution. A computer readable medium may take many forms, including but not limited to, non-volatile media, volatile media, and transmission media. Non-volatile media includes, for example, optical, magnetic disks, and magneto-optical disks, such as the hard disk or the removable media drive. Volatile media includes dynamic memory, such as the main memory. Transmission media includes coaxial cables, copper wire and fiber optics, including the wires that make up the bus. Transmission media may also take the form of acoustic or light waves, such as those generated during radio wave and infrared data communications.

As used herein the term "data network" or "network" shall mean an infrastructure capable of connecting two or more computers such as client devices either using wires or wirelessly allowing them to transmit and receive data. Non-limiting examples of data networks may include the internet or wireless networks or (i.e. a "wireless network") which may include Wifi and cellular networks. For example, a network may include a local area network (LAN), a wide area network (WAN) (e.g., the Internet), a mobile relay network, a metropolitan area network (MAN), an ad hoc network, a telephone network (e.g., a Public Switched Telephone Network (PSTN)), a cellular network, or a voice-over-IP (VoIP) network.

As used herein, the term "database" shall generally mean a digital collection of data or information. The present invention uses novel methods and processes to store, link, and modify information such digital images and videos and user profile information. For the purposes of the present disclosure, a database may be stored on a remote server and accessed by a client device through the internet (i.e., the database is in the cloud) or alternatively in some embodiments the database may be stored on the client device or remote computer itself (i.e., local storage). A "data store" as used herein may contain or comprise a database (i.e. information and data from a database may be recorded into a medium on a data store).

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

A novel system and methods for promoting medication adherence are discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

The present invention will now be described by example and through referencing the appended figures representing preferred and alternative embodiments. As perhaps best shown by FIG. 1, an illustrative example of some of the physical components which may comprise a system for promoting medication adherence ("the system") 100 according to some embodiments is presented. The system 100 is configured to facilitate the transfer of data and information between one or more access points 103, client devices 400, and servers 300 over a data network 105. A data store 308 accessible by the server 300 may contain one or more databases, such as a system database 106. The data may comprise any information that one or more users 101 desire to input into the system 100 including information describing one or more users 101, information describing the actions of one or more users 101, information requested by one or more users 101, information supplied by one or more users 101, and any other information which a user 101 may desire to input or enter into the system 100. In further embodiments, the information may include medical information, such as patient health information, patient medication compliance information, patient treatment compliance information, patient treatment plan information, medication information, healthcare provider information, and the like. In still further embodiments, the information may include financial incentive information such as coupons and special offers.

In this example, the system 100 comprises at least one client device 400 (but preferably more than two client devices 400) configured to be operated by one or more users 101. Client devices 400 can be mobile devices, such as laptops, tablet computers, personal digital assistants, smart phones, and the like, that are equipped with a wireless network interface capable of sending data to one or more servers 300 with access to one or more data stores 308 over a network 105 such as a wireless local area network (WLAN). Additionally, client devices 400 can be fixed devices, such as desktops, workstations, and the like, that are equipped with a wireless or wired network interface capable of sending data to one or more servers 300 with access to one or more data stores 308 over a wireless or wired local area network 105. The system 100 may be implemented on at least one client device 400 and/or server 300 programmed to perform one or more of the steps described herein. In some embodiments, more than one client device 400 and/or server 300 may be used, with each being programmed to carry out one or more steps of a method or process described herein.

The system 100 is configured to promote medication adherence by a user 101 while also providing information to that user 101 and/or to one or more other users 101. A user 101 may include a first user 101A and a second user 101B. A first user 101A may comprise an individual that desires to reduce or prevent symptoms of a disease, such as Glaucoma, for themselves and may also be referred to as a patient. For the purposes of this disclosure a first user or patient 101A may include individuals under the care of a second user or vision care provider 101B and individuals not currently under the care of a second user or vision care provider 101B. A second user 101B may comprise an individual that may provide vision care to one or more first users 101A and may also be referred to as a vision care provider, optometrist, eye doctor, or other healthcare provider. In preferred embodiments, the system 100 may provide information and/or incentives to a patient 101A while promoting medication adherence for the patient 101A. In further preferred embodiments, the system 100 may provide information on the actions and activities of the patient 101A to the vision care provider 101B while promoting medication adherence for the patient 101A.

In preferred embodiments, the system 100 may be configured to promote medication adherence by reproducing visual field scotomas (areas of blind spots corresponding to glaucomatous disease) on the display screen input/output (I/O) interface 404 of the client device 400 being used by a patient 101A. The visual field scotomas may be reproduced on the client device 400 by blacking out or otherwise obstructing portions of the display screen 404 to mimic how a person suffering from a particular vision would see the display screen. Preferably, the size, opacity, and/or shape of the defects reproduced on the display screen 404 would increase, decrease, or otherwise change based on the medication adherence actions of the patient 101A using the client device 400. For example, as patients 101A use their medication, visit the doctor, or perform other medication adherence activities, the appearance, size, opacity, shape, and/or location of the portions of the display screen 404 that are blacked out or otherwise obstructed may change to mimic actual real glaucomatous defects and disease progression to the patient 101A when viewing the display screen 404.

The ability of the patient 101A to adhere to daily medication use and compliance with doctor visits may determine the appearance of the scotomas represented on the display screen 404. The less adherent the patient 101A is by missing a compliance event, such as by not taking medication, missing doctor appointments, and the like, portions of the display screen 404A may become blacked out or otherwise obstructed and/or increase in size to depict the scotomas in advanced time to show the patient 101A what their visual field looks like or may become like. Because glaucoma is so insidious and patients 101A are not compliant with medication because of a lack of symptoms, the novel system 100 and methods disclosed are able to show patients 101A their vision field loss with realistic and scientific representations of scotomas. Optionally, the more adherent the patient 101A is by a performing compliance event, such as by taking medication, completing doctor appointments, and the like, portions of the display screen 404A may cease to become blacked out or otherwise obstructed and/or decrease in size to depict the shrinking or disappearance of scotomas in advanced time, even though this is not medically possible, to show the patient 101A that their compliance is having a positive effect by reducing disease progression. In still further embodiments, the activities of the patient 101A while using the system 100 may result in the patient 101A being provided incentive information, such as coupons and special offers which may be redeemed for discounts on medication, discounts on copays or office visit costs, and the like.

Figure 18:
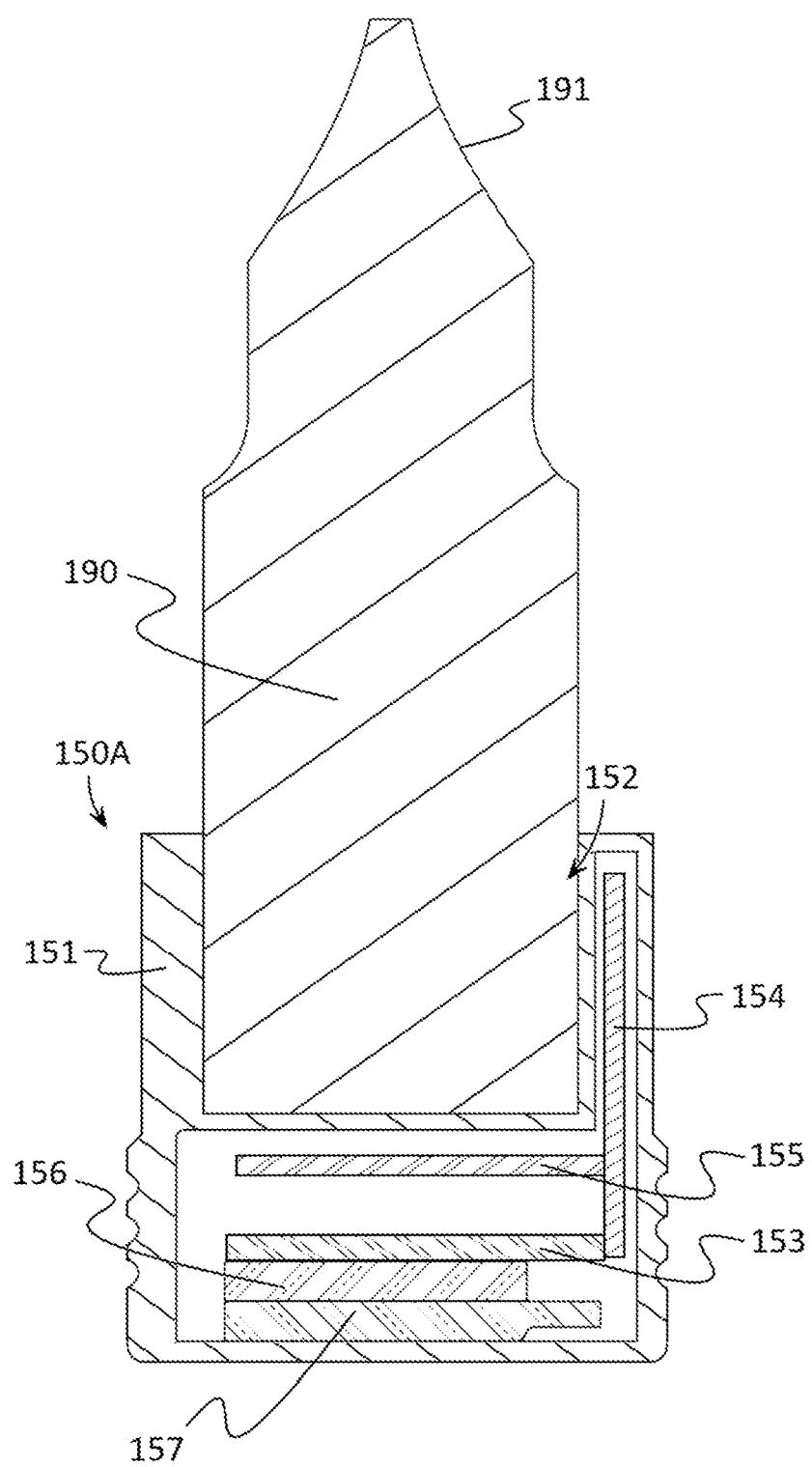
FIG. 18 shows a sectional elevation view of an example of a unibody of an exemplary medication adherence device coupled to a lower portion of a medicine container according to various embodiments described herein.
Figure 19:
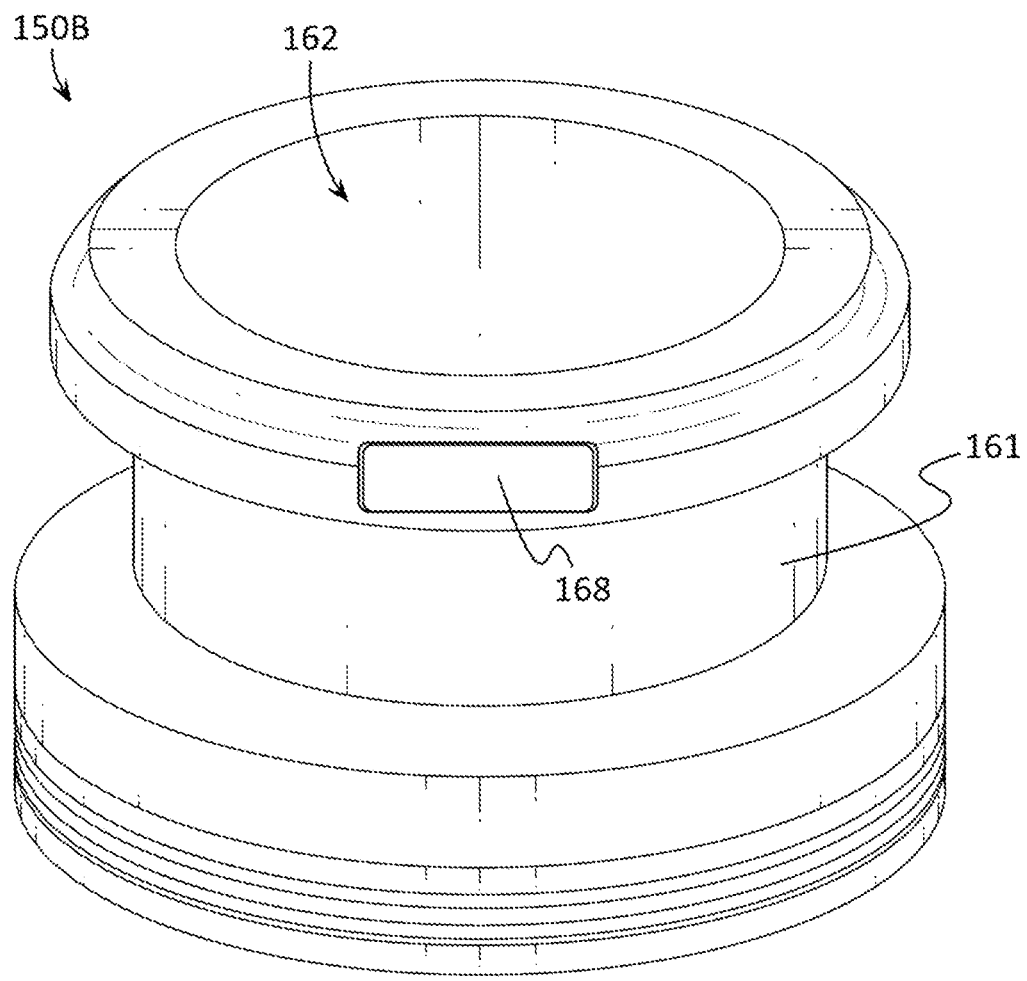
FIG. 19 depicts a perspective view of an example of a station of an exemplary medication adherence device according to various embodiments described herein.
Figure 20:
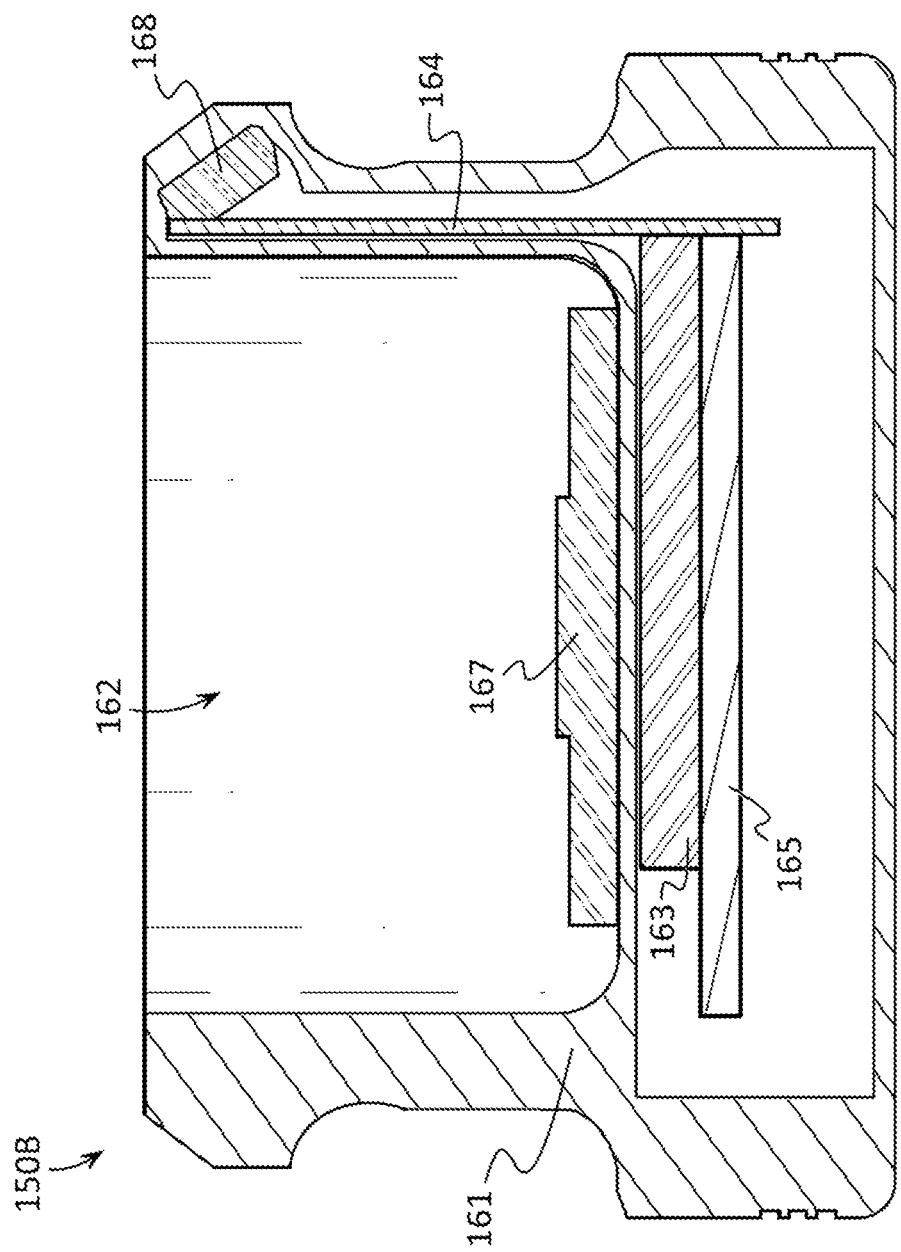
FIG. 20 illustrates a sectional elevation view of an example of a station of an exemplary medication adherence device according to various embodiments described herein.

While in some embodiments, the system 100 may receive medication access information that is self-reported by the patient 101A or a care giving party, via their client device 400, that describes if the patient 101A has taken or been administered the medication (performed a compliance event) corresponding to a provided reminder, in other embodiments, the system 100 may receive medication access information from a medication adherence device 150 (described in FIGS. 17-23) that may be coupled and uncoupled from a medicine container 190 of a medicine that has been prescribed to the patient 101A. Medication access information received from a medication adherence device 150 may comprise data describing motions or movements of a medicine container 190 that a unibody 150A of medication adherence device 150 may be coupled to, data describing the lack of motions or movements of a medicine container 190 that a unibody 150A of medication adherence device 150 may be coupled to, or any other information which may be recorded by an inertial measurement unit (IMU) 155 (FIGS. 18 and 22) of a medication adherence device 150.

Figure 2:
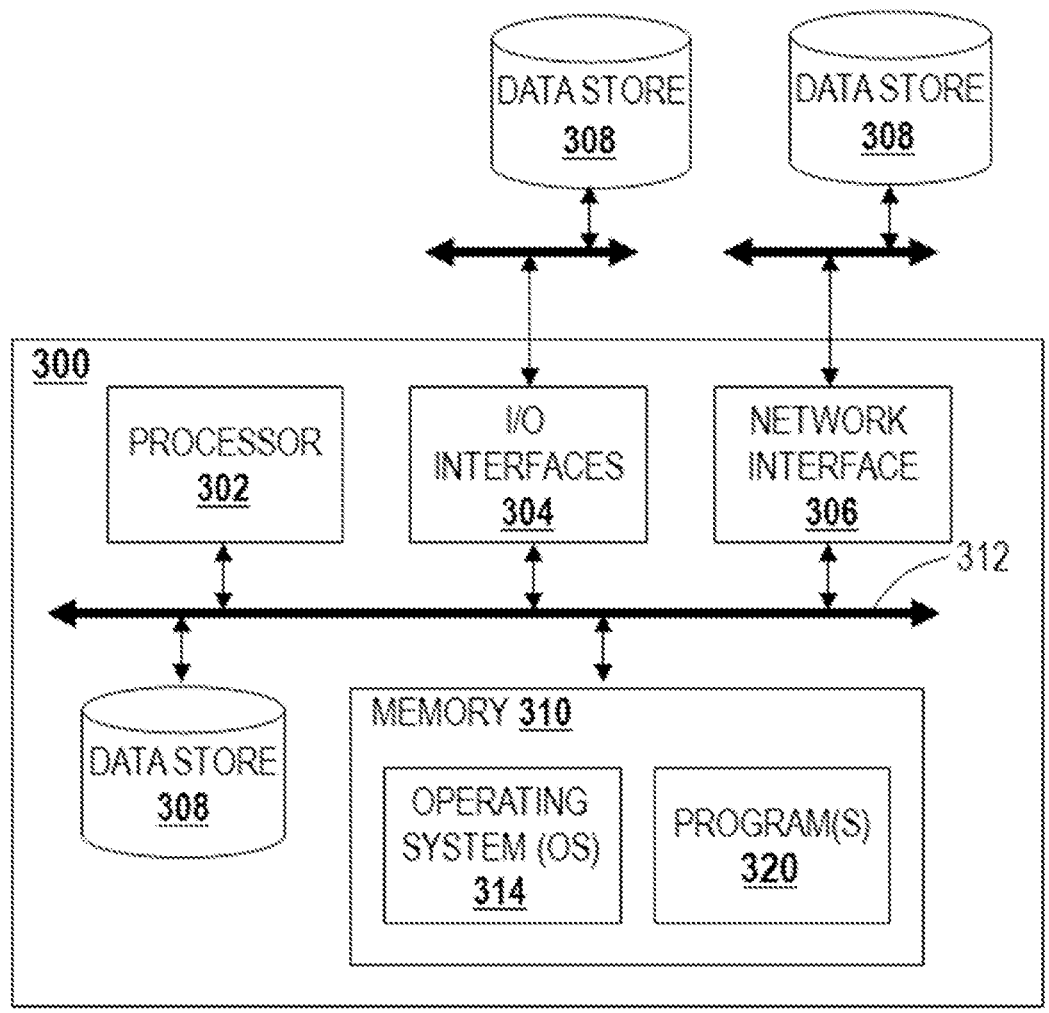
FIG. 2 illustrates a block diagram showing an example of a server which may be used by the system as described in various embodiments herein.

Referring now to FIG. 2, in an exemplary embodiment, a block diagram illustrates a server 300 of which one or more may be used in the system 100 or standalone. The server 300 may be a digital computer that, in terms of hardware architecture, generally includes a processor 302, input/output (I/O) interfaces 304, a network interface 306, a data store 308, and memory 310. It should be appreciated by those of ordinary skill in the art that FIG. 2 depicts the server 300 in an oversimplified manner, and a practical embodiment may include additional components and suitably configured processing logic to support known or conventional operating features that are not described in detail herein. The components (302, 304, 306, 308, and 310) are communicatively coupled via a local interface 312. The local interface 312 may be, for example but not limited to, one or more buses or other wired or wireless connections, as is known in the art. The local interface 312 may have additional elements, which are omitted for simplicity, such as controllers, buffers (caches), drivers, repeaters, and receivers, among many others, to enable communications. Further, the local interface 312 may include address, control, and/or data connections to enable appropriate communications among the aforementioned components.

The processor 302 is a hardware device for executing software instructions, such as the software instructions of the programs 320. The processor 302 may be any custom made or commercially available processor, a central processing unit (CPU), an auxiliary processor among several processors associated with the server 300, a semiconductor-based microprocessor (in the form of a microchip or chip set), or generally any device for executing software instructions. When the server 300 is in operation, the processor 302 is configured to execute software stored within the memory 310, to communicate data to and from the memory 310, and to generally control operations of the server 300 pursuant to the software instructions. The I/O interfaces 304 may be used to receive user input from and/or for providing system output to one or more devices or components. User input may be provided via, for example, a keyboard, touch pad, and/or a mouse. System output may be provided via a display device and a printer (not shown). I/O interfaces 304 may include, for example, a serial port, a parallel port, a small computer system interface (SCSI), a serial ATA (SATA), a fibre channel, Infiniband, iSCSI, a PCI Express interface (PCI-x), an infrared (IR) interface, a radio frequency (RF) interface, and/or a universal serial bus (USB) interface.

The network interface 306 may be used to enable the server 300 to communicate on a network, such as the Internet, the data network 105, the enterprise, and the like, etc. The network interface 306 may include, for example, an Ethernet card or adapter (e.g., 10BaseT, Fast Ethernet, Gigabit Ethernet, 10 GbE) or a wireless local area network (WLAN) card or adapter (e.g., 802.11a/b/g/n). The network interface 306 may include address, control, and/or data connections to enable appropriate communications on the network. A data store 308 may be used to store data. The data store 308 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 308 may incorporate electronic, magnetic, optical, and/or other types of storage media. In one example, the data store 308 may be located internal to the server 300 such as, for example, an internal hard drive connected to the local interface 312 in the server 300. Additionally in another embodiment, the data store 308 may be located external to the server 300 such as, for example, an external hard drive connected to the I/O interfaces 304 (e.g., SCSI or USB connection). In a further embodiment, the data store 308 may be connected to the server 300 through a network, such as, for example, a network attached file server.

The memory 310 may include any of volatile memory elements (e.g., random access memory (RAM, such as DRAM, SRAM, SDRAM, etc.)), nonvolatile memory elements (e.g., ROM, hard drive, tape, CDROM, etc.), and combinations thereof. Moreover, the memory 310 may incorporate electronic, magnetic, optical, and/or other types of storage media. Note that the memory 310 may have a distributed architecture, where various components are situated remotely from one another, but can be accessed by the processor 302. The software in memory 310 may include one or more software programs, each of which includes an ordered listing of executable instructions for implementing logical functions. The software in the memory 310 may include a suitable operating system (O/S) 314 and one or more programs 320.

The operating system 314 essentially controls the execution of other computer programs, such as the one or more programs 320, and provides scheduling, input-output control, file and data management, memory management, and communication control and related services. The operating system 314 may be, for example Windows NT, Windows 2000, Windows XP, Windows Vista, Windows 7, Windows 8, Windows 10, Windows Server 2003/2008 (all available from Microsoft, Corp. of Redmond, Wash.), Solaris (available from Sun Microsystems, Inc. of Palo Alto, Calif.), LINUX (or another UNIX variant) (available from Red Hat of Raleigh, N.C. and various other vendors), Android and variants thereof (available from Google, Inc. of Mountain View, Calif.), Apple OS X and variants thereof (available from Apple, Inc. of Cupertino, Calif.), or the like. The one or more programs 320 may be configured to implement the various processes, algorithms, methods, techniques, etc. described herein.

Figure 3:
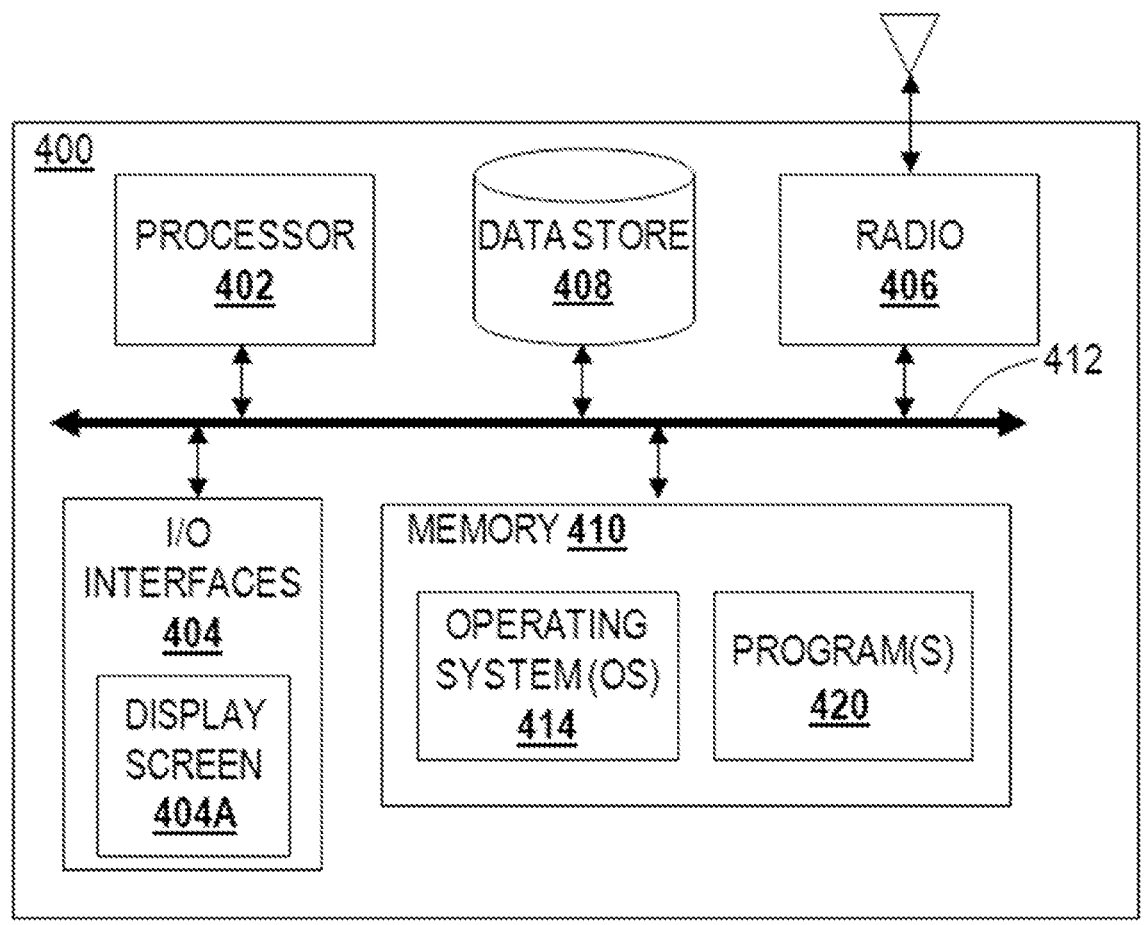
FIG. 3 shows a block diagram illustrating an example of a client device which may be used by the system as described in various embodiments herein.

Referring to FIG. 3, in an exemplary embodiment, a block diagram illustrates a client device 400 of which one or more may be used in the system 100 or the like. The client device 400 can be a digital device that, in terms of hardware architecture, generally includes a processor 402, input/output (I/O) interfaces 404, a radio 406, a data store 408, and memory 410. It should be appreciated by those of ordinary skill in the art that FIG. 3 depicts the client device 400 in an oversimplified manner, and a practical embodiment may include additional components and suitably configured processing logic to support known or conventional operating features that are not described in detail herein. The components (402, 404, 406, 408, and 410) are communicatively coupled via a local interface 412. The local interface 412 can be, for example but not limited to, one or more buses or other wired or wireless connections, as is known in the art. The local interface 412 can have additional elements, which are omitted for simplicity, such as controllers, buffers (caches), drivers, repeaters, and receivers, among many others, to enable communications. Further, the local interface 412 may include address, control, and/or data connections to enable appropriate communications among the aforementioned components.

The processor 402 is a hardware device for executing software instructions, such as the software instructions of the programs 420. The processor 402 can be any custom made or commercially available processor, a central processing unit (CPU), an auxiliary processor among several processors associated with the client device 400, a semiconductor-based microprocessor (in the form of a microchip or chip set), or generally any device for executing software instructions. When the client device 400 is in operation, the processor 402 is configured to execute software stored within the memory 410, to communicate data to and from the memory 410, and to generally control operations of the client device 400 pursuant to the software instructions. In an exemplary embodiment, the processor 402 may include a mobile optimized processor such as optimized for power consumption and mobile applications.

The I/O interfaces 404 can be used to receive data and user input and/or for providing system output. User input can be provided via a plurality of I/O interfaces 404, such as a keypad, a touch screen, a camera, a microphone, a scroll ball, a scroll bar, buttons, bar code scanner, voice recognition, eye gesture, and the like. System output can be provided via a display device type I/O interface 404 or display screen 404A, such as a liquid crystal display (LCD), touch screen, and the like. The I/O interfaces 404 can also include, for example, a serial port, a parallel port, a small computer system interface (SCSI), an infrared (IR) interface, a radio frequency (RF) interface, a universal serial bus (USB) interface, and the like. The I/O interfaces 404 can include a graphical user interface (GUI) that enables a user to interact with the client device 400. Additionally, the I/O interfaces 404 may be used to output notifications to a user and can include a speaker or other sound emitting device configured to emit audio notifications, a vibrational device configured to vibrate, shake, or produce any other series of rapid and repeated movements to produce haptic notifications, and/or a light emitting diode (LED) or other light emitting element which may be configured to illuminate to provide a visual notification.

The radio 406 enables wireless communication to an external access device or network. Any number of suitable wireless data communication protocols, techniques, or methodologies can be supported by the radio 406, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; Long Term Evolution (LTE); cellular/wireless/cordless telecommunication protocols (e.g. 3G/4G, etc.); wireless home network communication protocols; paging network protocols; magnetic induction; satellite data communication protocols; wireless hospital or health care facility network protocols such as those operating in the WMTS bands; GPRS; proprietary wireless data communication protocols such as variants of Wireless USB; and any other protocols for wireless communication. The data store 408 may be used to store data. The data store 408 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 408 may incorporate electronic, magnetic, optical, and/or other types of storage media.

The memory 410 may include any of volatile memory elements (e.g., random access memory (RAM, such as DRAM, SDRAM, etc.)), nonvolatile memory elements (e.g., ROM, hard drive, etc.), and combinations thereof. Moreover, the memory 410 may incorporate electronic, magnetic, optical, and/or other types of storage media. Note that the memory 410 may have a distributed architecture, where various components are situated remotely from one another, but can be accessed by the processor 402. The software in memory 410 can include one or more software programs, each of which includes an ordered listing of executable instructions for implementing logical functions. In the example of FIG. 3, the software in the memory system 410 includes a suitable operating system (O/S) 414 and programs 420.

The operating system 414 essentially controls the execution of other computer programs, and provides scheduling, input-output control, file and data management, memory management, and communication control and related services. The operating system 414 may be, for example, LINUX (or another UNIX variant), Android (available from Google), Symbian OS, Microsoft Windows CE, Microsoft Windows 7 Mobile, iOS (available from Apple, Inc.), webOS (available from Hewlett Packard), Blackberry OS (Available from Research in Motion), and the like. The programs 420 may include various applications, add-ons, etc. configured to provide end user functionality with the client device 400. For example, exemplary programs 420 may include, but not limited to, a web browser, social networking applications, streaming media applications, games, mapping and location applications, electronic mail applications, financial applications, and the like. In a typical example, the end user typically uses one or more of the programs 420 along with a network such as the system 100.

Figure 4:
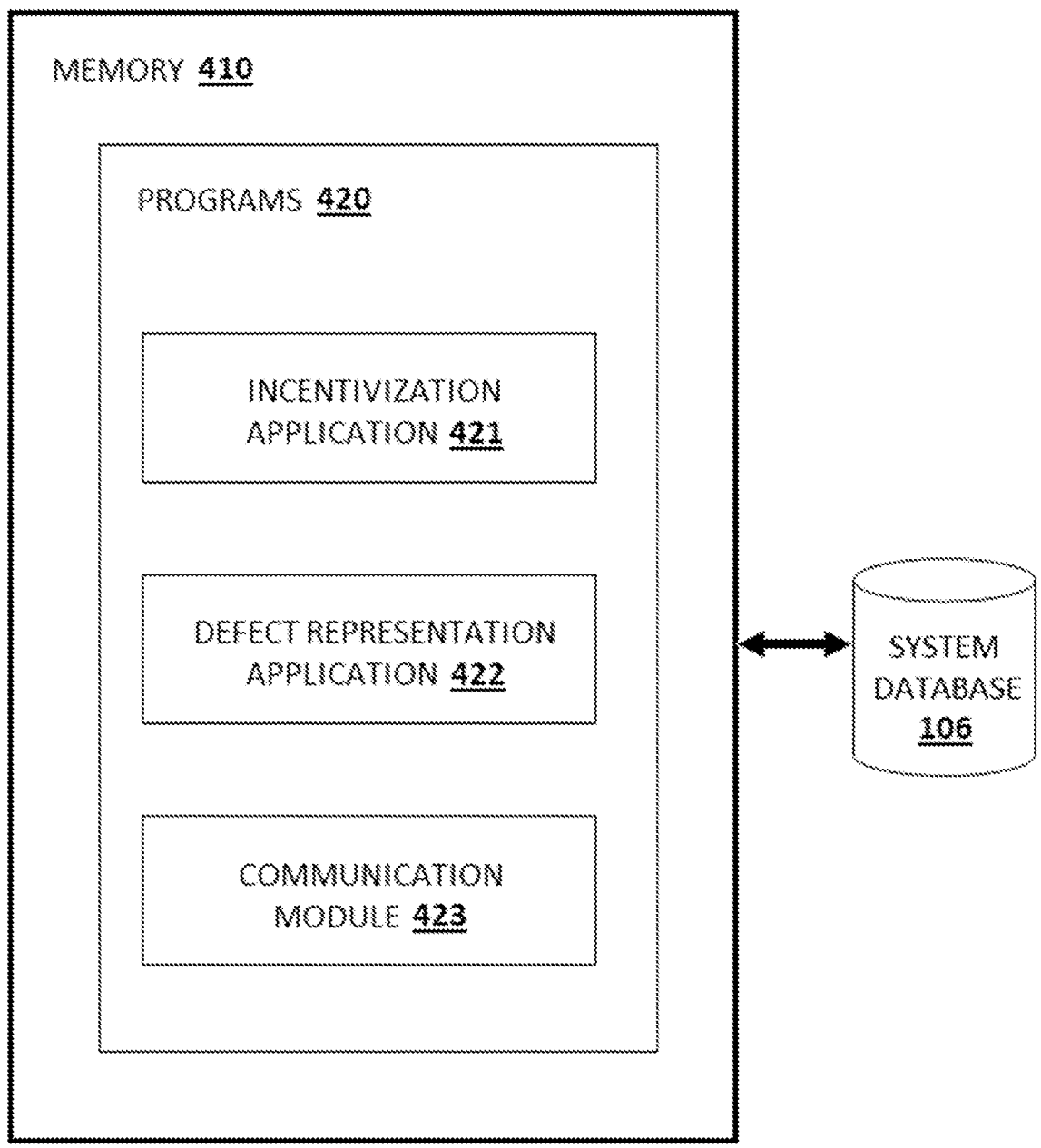
FIG. 4 depicts a block diagram illustrating some application modules which may function as software rules engines in a system for promoting medication adherence according to various embodiments described herein.

FIG. 4 depicts a block diagram showing some software rules engines which may be found in a system 100 and which may optionally be configured to run on a server 300 and/or a client device 400 according to various embodiments described herein. In some embodiments, one or more servers 300 and/or client devices 400 may be configured to run one or more software rules engines or programs such as an incentivization application 421, a defect representation application, and/or a communication module 423. In this embodiment, the software engines 421, 422, and 423, are configured to run on at least one client device 400. The client device 400 may be in electronic communication with a data store 308 comprising a database, such as a system database 106. The engines 421, 422, and 423, may read, write, or otherwise access data in the database of the data store 308. Additionally, data may be sent and received to and from one or more client devices 400 which may be in wired and/or wireless electronic communication with a server 300 through a network 105.

The system 100 may comprise a system database 106 stored on one or more data stores 308, 408, preferably accessible to the incentivization application 421 and/or optionally accessible to the defect representation application 422 and/or communication module 423. In some embodiments, the system database 106 may comprise data and information on one or more users 101 such as data describing one or more first users or patients 101A and second users or vision care providers.

Data describing a patient 101A may include data on the amount of time the patient has used system 100, data inputted by the patient 101A into the system such as access codes, incentives earned by the patient 101A, medication compliance data of the patient 101A, incentives redeemed by the patient 101A, information viewed by the patient 101A, information not viewed by the patient 101A, location of the patient 101A, one or more vision care providers 101B associated with a patient 101A, prescribed medications of the patient 101A, or any other information descriptive of a patient 101A and/or the activities of the patient 101A.

Data describing a vision care provider 101B may include data and information describing one or more patients 101A, such as intraocular pressure (TOP), that a vision care provider 101B may input, and information desired to be displayed to one or more patients 101A that a vision care provider 101B may input, vision care provider 101B contact information and other information describing a vision care provider 101B, incentives desired to be displayed to one or more patients 101A that a vision care provider 101B may select or input, one or more patients 101A associated with a vision care provider 101B, medications prescribed to a patient 101A by the vision care provider 101B, medication directions, or any other information descriptive of a vision care provider 101B and/or the activities of the vision care provider 101B.

In preferred embodiments, a system database 106 may comprise data describing treatment plan information for each first user or patient 101A of the system. Treatment plan information for a patient 101A may comprise information describing a daily number of compliance events for a medication of the first user or patient 101A. A compliance event may generally describe a dose of a medication and a time or time period at which the dose of a medication is to be taken by or otherwise provided to the patient 101A. For example, a treatment plan for a first medication may include that one drop of a first medication is to be instilled into each eye of the patient 101A three times a day approximately eight hours apart at approximately 6 AM, 2 PM, and 10 PM and each dose may be taken in a time period such as plus or minus one hour to each dosing time. In this example, the treatment plan comprises three daily compliance events for the medication so that if the medication is not used within plus or minus one hour to a dosing time, the system 100 may record this as a missed compliance event. Conversely, if the medication is used within plus or minus one hour to a dosing time, the system 100 may record this as a performed compliance event.

In further preferred embodiments, the system 100 may be configured to track or tally a cumulative number of missed and/or performed compliance events for each patient 101A and preferably for each medication of each patient 101A in one or more system databases 106. The cumulative number of missed and/or performed compliance events for each patient 101A may be stored in one or more system databases 106 which may be in a data store 408 of a client device 400 associated with the patient 101A and/or which may be in a data store 308 of a server 300 of the system 300. Data describing missed and/or performed compliance events for each patient 101A may be synced between system databases 106 when client devices 400 and servers 300 are in communication.

In further preferred embodiments, the system 100 may be configured to track the intraocular pressure of one or both eyes for each patient 101A of the system 100 in one or more system databases 106. Preferably, intraocular pressure measurements may be provided to the system 100 via the treatment plan information which may be created by a second user or vision care provider 101B or their agent, although the intraocular pressure of one or both eyes for a patient 101A may be provided or uploaded to the system 100 via any other method.

The incentivization application 421 may be configured to send, receive, access, modify, and otherwise manipulate data in a system database 106. In some embodiments, the incentivization application 421 may be configured to track and record activities of a patient 101A while using the system 100. In some embodiments, the incentivization application 421 may track activities by a patient 101A such as taking medication, completing doctor appointments, using a client device 400 of the system 100 and the like, which may describe how adherent the patient 101A is to medication and treatment. In further embodiments, the incentivization application 421 may track activities by a patient 101A such as not taking medication, not completing doctor appointments, not using a client device 400 of the system 100 and the like, which may describe how adherent the patient 101A is to medication and treatment.

In some embodiments, the incentivization application 421 may be configured to associate one or more patients 101A with one or more vision care providers 101B. Once a patient 101A is associated with the vision care provider 101B, the incentivization application 421 may allow data associated with the vision care provider 101B to be provided to the patient 101A, such as through the client device 400 of the patient 101A, and/or data associated with the patient 101A to be provided to the vision care provider 101B, such as through the client device 400 of the vision care provider 101B.

In some embodiments, the incentivization application 421 may be configured to receive data provided by or selected by a vision care provider 101B and to associate that data with the vision care provider 101B in the system database 106. The data or information may include financial incentives, such as coupons, offers, discounts, medical information of a patient 101A, medication of a patient 101A, medication and/or treatment directions for a patient 101A and the like, which may optionally be provided to a patient 101A which is associated with the vision care provider 101B in the system database 106. Also, the data may include notices, such as appointment reminders, communications, such as messages to one or more patients 101A, or any other type of message a vision care provider 101B may desire to have associated with themselves in the system database 106.

In some embodiments, the incentivization application 421 may be configured to retrieve data associated with one or more patients 101A in the system database 106 and to provide the data to a vision care provider 101B such as through the client device 400 of the vision care provider 101B. In preferred embodiments, the incentivization application 421 may be configured to retrieve and display to a vision care provider 101B data associated with one or more patients that are associated with that vision care provider 101B.

The defect representation application 422 may be configured to reproduce visual field scotomas (areas of blind spots corresponding to glaucomatous disease) on the display screen input/output (I/O) interface 404 of the client device 400 being used by a patient 101A. The visual field scotomas may be reproduced on the client device 400 by blacking out or otherwise obstructing portions of the display screen 404 to mimic how a person suffering from a particular vision would see the display screen. The defect representation application 422 may determine if a patient 101A has missed and/or performed one or more compliance events, and preferably based on a cumulative number of missed compliance events, the defect representation application 422 may form one or more blind spots 110 on a display screen 404 which may visually obscure information that would otherwise be visible on the display screen 404 where the blind spot 110 is. The defect representation application 422 may be configured to control the size, opacity, position, and/or shape of one or more blind spots 110 or defects reproduced on the display screen 404 to increase, decrease, or otherwise change based on the medication adherence actions of the patient 101A using the client device 400 which may be provided to the defect representation application 422 by the incentivization application 421. The defect representation application 422 may be configured to control the individual pixels of the display screen 404 to reproduce visual field scotomas on the display screen 404. Preferably, blind spots 110 produced on a display screen 404A of a client device 400 may generally comprise a shape of a glaucoma associated scotoma as shown in FIGS. 8-16.

The defect representation application 422 may be configured to generate one or more blind spots 110 on the display screen 404A of the client device 400 of the user 101A based on a cumulative number of missed compliance events and/or a cumulative number of performed compliance events. In some embodiments, the defect representation application 422 may be configured to generate one or more blind spots 110 on the display screen 404A in response or in proportion to an increasing cumulative number of missed compliance events for a patient 101A on their respective client device 400. In further embodiments, the defect representation application 422 may be configured to increase the size of one or more blind spots 110 on the display screen 404A in response or in proportion to an increasing cumulative number of missed compliance events for a patient 101A on their respective client device 400. In still further embodiments, the defect representation application 422 may be configured to increase the opacity (such as from being somewhat transparent so some information can be seen through or in spite of the blind spot 110 to being less transparent) of one or more blind spots 110 on the display screen 404A in response or in proportion to an increasing cumulative number of missed compliance events for a patient 101A on their respective client device 400. In some embodiments, the defect representation application 422 may be configured to increase the size and/or opacity of one or more blind spots 110 on a display screen 404A by approximately between one and 100 pixels, and preferably between one and five pixels, for each missed compliance event.

In still further embodiments, the defect representation application 422 may be configured to cease generating one or more blind spots 110 on the display screen 404A in response or in proportion to an increasing cumulative number of performed compliance events for a patient 101A on their respective client device 400. In yet further embodiments, the defect representation application 422 may be configured to decrease the size of one or more blind spots 110 on the display screen 404A in response or in proportion to an increasing cumulative number of performed compliance events for a patient 101A on their respective client device 400. In still further embodiments, the defect representation application 422 may be configured to decrease the opacity (such as from being less transparent to being more transparent so more information can be seen through or in spite of the blind spot 110) of one or more blind spots 110 on the display screen 404A in response or in proportion to an increasing cumulative number of performed compliance events for a patient 101A on their respective client device 400. In some embodiments, the defect representation application 422 may be configured to decrease the size and/or opacity of one or more blind spots 110 on a display screen 404A by approximately between one and 100 pixels, and preferably between one and five pixels, for each missed compliance event.

In still further embodiments, the defect representation application 422 may be configured to generate one or more blind spots 110 on the display screen 404A of the client device 400 of the user 101A based on an intraocular pressure measurement for the patient 101A increasing from the previous most recent intraocular pressure measurement to the most recent intraocular pressure measurement. In some embodiments, the defect representation application 422 may be configured to generate one or more blind spots 110 on the display screen 404A in response or in proportion to an increase between a first intraocular pressure measurement (previous most recent intraocular pressure measurement) and a second intraocular pressure measurement (most recent intraocular pressure measurement) for a patient 101A on their respective client device 400. In further embodiments, the defect representation application 422 may be configured to increase the size and/or opacity of one or more blind spots 110 on the display screen 404A in response or in proportion to an increase between a first intraocular pressure measurement (previous most recent intraocular pressure measurement) and a second intraocular pressure measurement (most recent intraocular pressure measurement) for a patient 101A on their respective client device 400.

In yet further embodiments, the defect representation application 422 may be configured to cease generating one or more blind spots 110 on the display screen 404A of the client device 400 of the user 101A based on an intraocular pressure measurement for the patient 101A decreasing from the previous most recent intraocular pressure measurement to the most recent intraocular pressure measurement. In still further embodiments, the defect representation application 422 may be configured to cease generating one or more blind spots 110 on the display screen 404A in response or in proportion to a decrease between a first intraocular pressure measurement (previous most recent intraocular pressure measurement) and a second intraocular pressure measurement (most recent intraocular pressure measurement) for a patient 101A on their respective client device 400. In further embodiments, the defect representation application 422 may be configured to decrease the size and/or opacity of one or more blind spots 110 on the display screen 404A in response or in proportion to a decrease between a first intraocular pressure measurement (previous most recent intraocular pressure measurement) and a second intraocular pressure measurement (most recent intraocular pressure measurement) for a patient 101A on their respective client device 400.

The communication module 423 be configured to govern electronic communication between one or more client devices 400, data stores 308, 408, and/or severs 300. Data from severs 300, data stores 308, 408, and client devices 400 may be received by the communication module 423 which may then electronically communicate the data to the incentivization application 421 and/or defect representation application 422. Likewise, data from the incentivization application 421 and/or defect representation application 422 may be received by the communication module 423 which may then electronically communicate the data to severs 300, data stores 308, 408, and client devices 400. In some embodiments, the communication module 423 may govern the electronic communication by initiating, maintaining, reestablishing, and terminating electronic communication between one or more data stores 308,408, client devices 400, and servers 300. In further embodiments, the communication module 423 may control the network interface 306 of the server 300 and/or radio 406 of a client device 400 to send and receive data to and from one or more data stores 308, client devices 400, and other servers 300 through a network connection 104 over a network 105.

Figure 5:
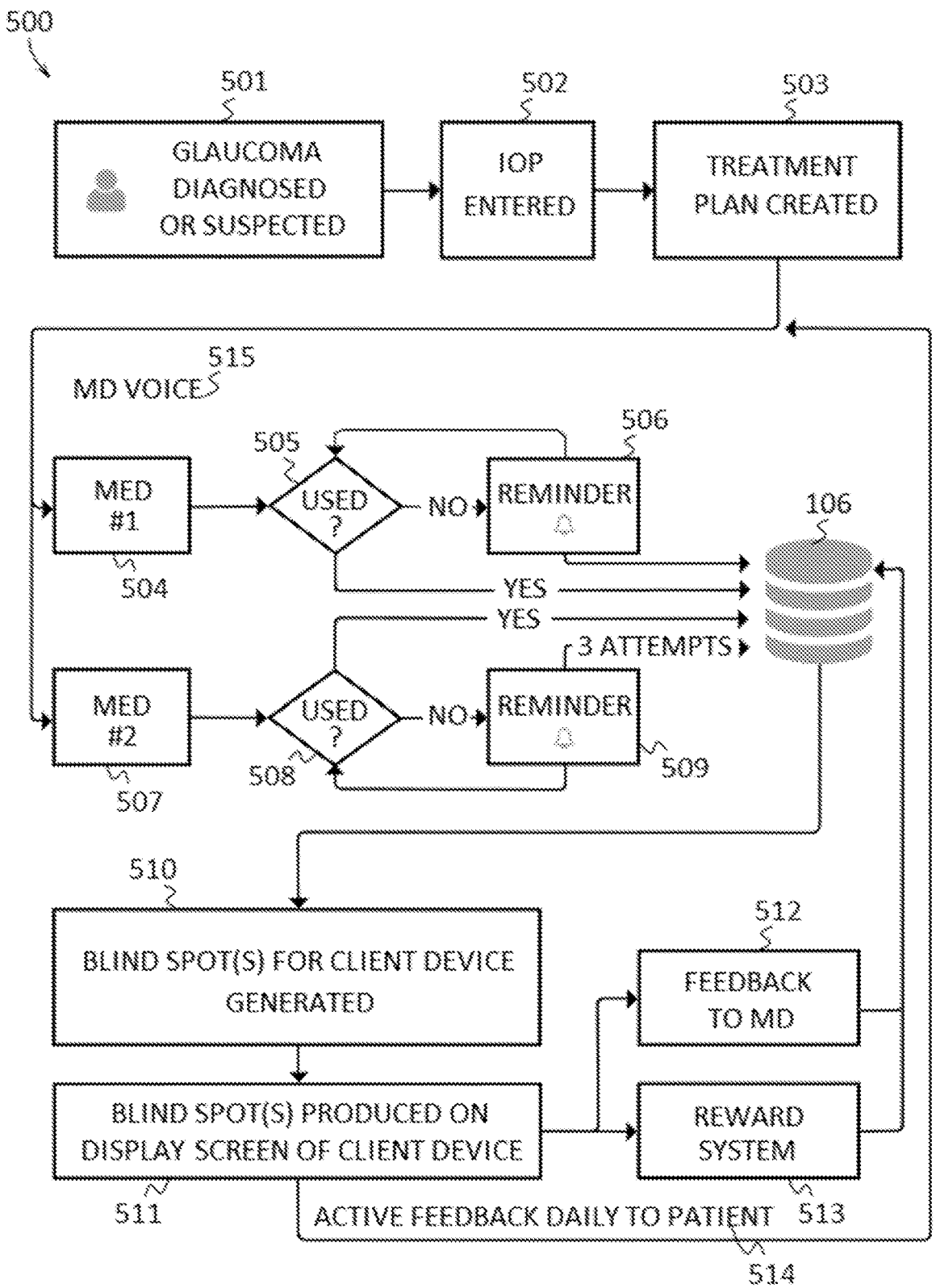
FIG. 5 illustrates a block diagram of an example of a method of promoting medication adherence according to various embodiments described herein.

FIG. 5 illustrates a block diagram of an example of a method of promoting medication adherence ("the method")

500 according to various embodiments described herein. The method 500 may be used to provide information to a patient 101A and vision care provider 101B for promoting the medication adherence of the patient 101A. One or more steps of the method may be performed by an incentivization application 421, a defect representation application 422, and/or a communication module 423 which may be performed by a computing device processor 302 of a server 300 and/or a computing device processor 402 of a client device 400.

In some embodiments, the method 500 may start and the vision care provider 101B may diagnose the patient 101A as being either a glaucoma suspect or glaucoma patient in step 501. The term glaucoma may include all variations of the optic neuropathy, i.e. primary open glaucoma, narrow angle glaucoma, low tension glaucoma, normal tension glaucoma, pigmentary dispersion glaucoma, uveitic glaucoma, pseudo-exfoliation glaucoma, neovascular glaucoma, etc.

In step 502, the patient's 101A intraocular pressure (TOP) information and/or other medical information describing the patient 101A may be entered by the vision care provider 101B. Information and input may be received through a keyboard I/O interface 404, a microphone I/O interface 404, or any other I/O interface 404 of a client device 400 operated by the vision care provider 101B which may then be communicated to an incentivization application 421 by a communication module 423. In some embodiments, the information may include: incentives, such as discounts, special offers, coupons, and the like; educational information, such as information on glaucoma, and other health and wellness information; information describing the vision care provider 101B, such as the vision care provider's 101B contact information (such as office telephone number and website address), credentials, insurance plans accepted, address, pricing information; or any other information which may be provided by a vision care provider 101B.

Continuing to step 503, the current medication noted or prescribed by the vision care provider 101B to the patient 101A may be entered by the vision care provider 101B as treatment plan information preferably comprising a daily number of compliance events for a medication of a patient 101A and preferably comprising an intraocular pressure measurement for the patient 101A. Information and input may be received through a keyboard I/O interface 404, a microphone I/O interface 404, or any other I/O interface 404 of a client device 400 operated by the vision care provider 101B which may then be communicated to an incentivization application 421 by a communication module 423.

In step 504, the user 101A may be presented with a first medication that was prescribed to them by the vision care provider 101B on the client device 400 by the incentivization application 421. At decision block 505, the patient 101A may then indicate that they have taken the medication and data describing this may be sent to a system database 106 accessible to the system 100 by the communication module 423. At decision block 505 if the patient 101A indicates that they have not taken the medication, the method 500 may proceed to providing a reminder system 506 comprising one or more audio and/or visual reminders that may be provided to the patient 101A through an I/O interface of the client device 400 by the incentivization application 421, where at a later point in time, the patient 101A will be again presented with a medication confirmation. If after 3 attempts or a number of attempts designated by the user 101A or provider 101B, the patient 101A has not used the medication, this information may be sent to a system database 106 accessible to the system 100 by the communication module 423. Optionally, the vision care provider's 101B voice 515 or another alternate voice is recorded which may then be incorporated. The voice may be used periodically, such as throughout the day, to remind the patient 101A to use their medication.

In step 507, the user 101A may be presented with a second medication that was prescribed to them by the vision care provider 101B on the client device 400 by the incentivization application 421. At decision block 508, the patient 101A may then indicate that they have taken the medication and data describing this may be sent to a system database 106 accessible to the system 100 by the communication module 423. At decision block 508 if the patient 101A indicates that they have not taken the medication, the method may proceed to providing a reminder system 509 comprising one or more audio and/or visual reminders may be provided to the patient 101A through an I/O interface of the client device 400 by the incentivization application 421, where at a later point in time, the patient 101A will be again presented with a medication confirmation. If after 3 attempts or a number of attempts designated by the user 101A or provider 101B, the patient 101A has not used the medication, this information may be sent to a system database 106 accessible to the system 100 by the communication module 423. Optionally, the vision care provider's 101B voice 515 or another alternate voice is recorded which may then be incorporated. The voice may be used periodically, such as throughout the day, to remind the patient 101A to use their medication.

In step 510, the medication adherence information may be used to generate representative scotomas or blind spots 110 based upon the adherence to the medication(s) and/or based on any other actions by the patient 101A. Optionally, the information may be collected and distributed by a central server 300. Representative examples of blind spots 110 displayed on the display screen 404 of a client device are shown in FIGS. 8-15. Blind spots 110 may be formed on the display screen 404A of the client device 400 of the user 101A by a defect representation application 422 with a lesser number of missed compliance events or other affirmative medication adherence information used to form smaller blind spots 110 on the display screen 404A and a greater number of missed compliance events or other negative medication adherence information used to form larger blind spots 110 on the display screen 404A. For example, a blind spot 110 may be formed on the display screen 404A by the defect representation application 422 with a single pixel square of scotoma being generated per missed compliance event to generate the perceived scotoma. The rate of "blindness" or the amount of the display screen 404A obscured by blind spots 110 may be much more rapid than that seen in the progression of typical glaucoma. This increased rate of scotoma formation will demonstrate to the patient 101A their peripheral vision loss. The size and/or opacity of a blind spot 110 generated on the display screen 404A may increase by any number of pixels and/or intensity level, such as one pixel and/or one intensity level, every time a missed compliance event of the patient 101A is recorded. An intensity level may describe a relative change in the appearance of a blind spot 110 on a display screen. For example, an increase of one intensity level may result in a blind spot 110 being one percent more opaque than previously generated. In some embodiments, a blind spot 110 may be increased or decreased between one and two hundred fifty six intensity levels so that the blind spot 110 may be generated between one and two hundred fifty six percent more or less opaque, respectively, than previously generated. A blind spot 110 may increase in size, opacity, and/or shape preferably as shown by one of the exemplary blind spots 110 shaped as various physiologic glaucoma associated scotomas illustrated in FIGS. 8-16, although a blind spot 110 may be configured with any size, opacity, and/or shape. Optionally, as patients 101A complete or perform compliance events, the number of pixels and/or the intensity levels in one or more blind spots 110 may be reduced.

In step 511 the one or more blind spots 110 may be positioned on the display screen 404 of the client device 400 of the patient 101A by the defect representation application 422. In some embodiments, this may include gamification wherein the blind spots 110 may be positioned on the display screen 404 of the client device 400 which is being used for gaming or other entertainment or amusement purposes. Gamification is the term applied to using games to increase a form of adherence to medication use. Gamification is the use of game elements and game design techniques in a non-game context. Game elements are not the game itself, but the use of points, quests, avatars, resource collection, progression, social graph, and levels. In some embodiments, blind spots 110 may be configured in the shape of actual glaucoma scotomas on proprietary games, as well as games available as free domain. For example, the blind spots 110 in the shape of scotomas may appear in a shooting game, a shape fitting tetris type game, a driving game, and a bird navigating game during gamification.

The blind spots 110 may obscure the patient's 101A ability to observe portions of the game displayed on the client device 400 thereby hindering the patient's ability to play the game. In further embodiments, this may include gamblification wherein the blind spots 110 may be positioned on the display screen 404 of the client device 400 which is being used for gambling games or other wagering entertainment or amusement purposes. The blind spots 110 may obscure the patient's 101A ability to observe portions of the gambling games displayed on the client device 400 thereby hindering the patient's ability to play the gambling games. In further embodiments, feedback may be provided to the patient 101A, such as daily, in step 514.

Optionally, the method 500 may proceed to step 512 in which periodic, such as monthly or quarterly, feedback and other patient compliance information may be provided to the vision care provider 101B by the incentivization application 421. This information may include patient compliance with medication regimes and any other information describing the activities of the patient 101A while using the system 100. Monthly and quarterly feedback may be provided to the vision care provider 101B and relevant parties to include insurance companies, medical groups, the pharmacy, etc. as to the compliance of the patient 101B. This compliance may be calculated as an overall percentage of: Total doses taken/Total doses prescribed during a time period such as 1 week, 1 month, 3 months, or the like.

Optionally, the method 500 may proceed to step 513 in which incentive or reward information may be provided to patient 101A upon completing medication compliance or other activities with the system 100 by the incentivization application 421. This incentive information may include coupons and special offers which may be redeemed for discounts on medication, discounts on copays or office visit costs, and the like. Upon completion of steps 512, 513, and/or 514, the method may continue to any previously discussed step or the method 500 may finish.

Figure 6:
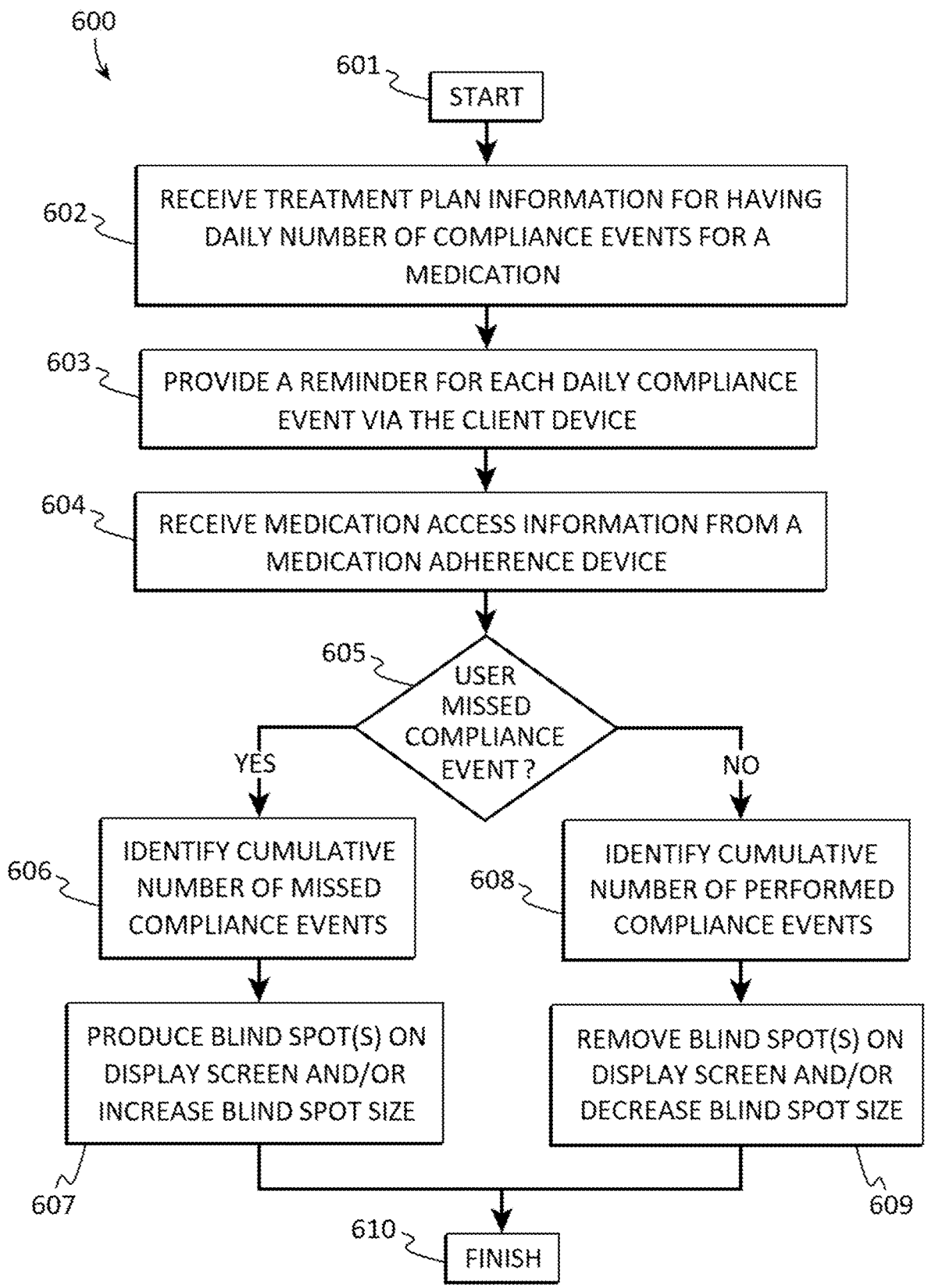
FIG. 6 shows a block diagram of an example of a method for promoting medication adherence by a user of a client device based on the medication adherence history of the user according to various embodiments described herein

FIG. 6 shows a block diagram of an example of a method for promoting medication adherence by a user of a client device based on the medication adherence history of the user ("the method 600) according to various embodiments described herein. The method 600 may be used to provide information to a patient 101A and vision care provider 101B for promoting the medication adherence of the patient 101A and optionally information may be provided by a medication adherence device 150. One or more steps of the method 600 may be performed by an incentivization application 421, a defect representation application 422, and/or a communication module 423 which may be performed by a computing device processor 302 of a server 300 and/or a computing device processor 402 of a client device 400. In some embodiments, the method 600 may be used to complete step 502 for the input of intraocular pressure (TOP) of the method 500 of FIG. 5. A vision care provider 101B may enter the intraocular pressure for both the right and left eye of the patient 101A, or any other medical information, on a client device 400. The vision care provider 101B may enter this data at every visit the patient 101A makes to the office as a vital sign of the eye. This data may be transmitted to one or more servers 300 and/or client devices 400.

In some embodiments, the method 600 may start and the vision care provider 101B may diagnose the patient 101A as being either a glaucoma suspect or glaucoma patient. The term glaucoma may include all variations of the optic neuropathy, i.e. primary open glaucoma, narrow angle glaucoma, low tension glaucoma, normal tension glaucoma, pigmentary dispersion glaucoma, uveitic glaucoma, pseudoexfoliation glaucoma, neovascular glaucoma, etc. The vision care provider 101B may provide treatment plan information via a client device 400 so that treatment plan information may be received by the system 100 in step 602. In preferred embodiments, the treatment plan information may include a daily number of compliance events for a medication for the patient 101A. In further preferred embodiments, the treatment plan information may include information describing one or more intraocular pressure measurements of an eye of the patient 101A, such as a first intraocular pressure measurement of an eye of the patient 101A and a second intraocular pressure measurement of the eye of the patient 101A. The treatment plan information may be communicated to an incentivization application 421 by a communication module 423. In some embodiments, the treatment plan information may include: incentives, such as discounts, special offers, coupons, and the like; educational information, such as information on glaucoma, and other health and wellness information; information describing the vision care provider 101B, such as the vision care provider's 101B contact information (such as office telephone number and website address), credentials, insurance plans accepted, address, pricing information; or any other information which may be provided by a vision care provider 101B.

In step 603, a reminder may be provided to the patient 101A for each daily compliance event via the respective client device 400 of the patient 101A. Preferably, the reminder may comprise a visual reminder displayed on the display screen 404A optionally comprising a picture of the medication, an audible reminder provided by a speaker-type IO interface 404 optionally comprising a tone, a vocal message, song, or the like, and/or a tactile reminder provided by a vibration-type I/O interface 404.

While in some embodiments, the system 100 may receive medication access information that is self-reported by the patient 101A or a care giving party via their client device 400 that describes if the patient 101A has taken or been administered the medication (performed a compliance event) corresponding to a provided reminder, in other embodiments, the system 100 may receive medication access information from a medication adherence device 150 as described in FIGS. 17-23. Medication access information received from a medication adherence device 150 may comprise data describing motions or movements of a medicine container 190 that a unibody 150A of medication adherence device 150 may be coupled to, data describing the lack of motions or movements of a medicine container 190 that a unibody 150A of medication adherence device 150 may be coupled to, or any other information which may be recorded by an inertial measurement unit (IMU) 155 (FIG. 22) of a medication adherence device 150. Preferably, each medication that is prescribed to the patient 101A may comprise a medication adherence device 150 with a unibody 150A configured to be removably coupled to a medicine container 190. In further embodiments, the medication adherence device 150 may be configured to generate medication access information when the unibody 150 that is coupled to a medicine container 190 is moved in a time period associated with the reminder and when the unibody 150 that is coupled to a medicine container 190 is not moved in a time period associated with the reminder. An example time period may be plus or minus fifteen minutes although any other time period may be associated with the reminder. In further embodiments, the medication adherence device 150 may include an inertial measurement unit (IMU) 155 which may record positional or orientation information as movement data which may be processed by the system 100 and used to generate medication access information.

In decision block 605, the defect representation application 422 may determine if the patient or first user 101A has missed a compliance event. If the defect representation application 422 determines that the patient or first user 101A has not missed a compliance event then the defect representation application 422 may determine that the patient or first user 101A has performed the compliance event. In some embodiments, the defect representation application 422 may determine if the patient or first user 101A has missed a compliance event using self-reported medication access information provided by the patient 101A via their client device 400. In preferred embodiments, the defect representation application 422 may determine if the patient or first user 101A has missed a compliance event using medication access information provided by a medication adherence device 150. For example, if a inertial measurement unit (IMU) 155 provided movement information, positional information, or the like that indicates that the medication adherence device 150 was not moved in one or more motions that are associated with the medication adherence device 150 being uncoupled from the medicine container 190 or motions that are associated with a patient 101A using the medication in a time period associated with a reminder, the defect representation application 422 may determine that the patient or first user 101A has missed a compliance event. Conversely, if a inertial measurement unit (IMU) 155 provided movement information, positional information, or the like that indicates that the medication adherence device 150 was moved in one or more motions that are associated with the medication adherence device 150 being uncoupled from the medicine container 190 or motions that are associated with a patient 101A using the medication in a time period associated with a reminder, the defect representation application 422 may determine that the patient or first user 101A has performed a compliance event.

In step 606, the defect representation application 422 may identify cumulative number of missed compliance events. Preferably, the defect representation application 422 may track or tally the number of missed compliance events as determined in decision block 605.

Continuing to step 607, the defect representation application 422 may produce one or more blind spots on the display screen 404A of the client device 400 of the patient 101A based on the cumulative number of missed compliance events identified in step 606. In preferred embodiments, the defect representation application 422 may produce one or more blind spots on the display screen 404A in which a blind spot 110 increases in size in proportion to an increasing cumulative number of missed compliance events identified in step 606 versus a blind spot 110 produced when the cumulative number of missed compliance events was a lesser number. In further embodiments, the defect representation application 422 may increase the size of a blind spot 110 produced on the display screen 404A by approximately between one and one hundred pixels, and more preferably between one and five pixels, for each missed compliance event. In still further embodiments, the defect representation application 422 may increase the opacity of a blind spot 110 produced on the display screen 404A by approximately between one and one hundred pixels, and more preferably between one and five pixels, and/or between one and two hundred fifty-six intensity levels for each missed compliance event.

In optional step 608, the defect representation application 422 may identify cumulative number of performed compliance events. Preferably, the defect representation application 422 may track or tally the number of performed compliance events as determined in decision block 605.

Continuing to optional step 609, the defect representation application 422 may remove one or more blind spots 110, decrease the size of a blind spot 110, and/or decrease the intensity level of a blind spot 110 produced on the display screen 404A of the client device 400 of the patient 101A based on the cumulative number of performed compliance events identified in step 608. In preferred embodiments, the defect representation application 422 may produce one or more blind spots on the display screen 404A in which a blind spot 110 decreases in size and/or opacity in proportion to an increasing cumulative number of performed compliance events identified in step 606 versus a blind spot 110 produced when the cumulative number of performed compliance events was a lesser number. In further embodiments, the defect representation application 422 may decrease the size and/or opacity of a blind spot 110 produced on the display screen 404A by approximately between one and one hundred pixels, and preferably between one and five pixels, and/or between one and two hundred fifty-six intensity levels for each performed compliance event. After step 607 and/or after optional step 609, the method 600 may finish 610.

Figure 7:
FIG. 7 depicts an example of a method of displaying medication data to a user for promoting medication adherence according to various embodiments described herein.

FIG. 7 depicts an example of a method of displaying medication data to a user for promoting medication adherence ("the method") 700 according to various embodiments described herein. The client device 400 of the patient 101A may display a reminder, comprising information describing the medication that the patient 101A is supposed to take, to facilitate the ability of the patient 101A to recognize the medication associated with a compliance event. Preferably, a picture of the medication container and packaging of a compliance event, may be displayed on the display screen 404 of the client device 400. For example, a picture of the medication bottle and the box or packaging of the medication bottle may be displayed on the display screen 404 of the client device 400 during the reminder. In further embodiments, portions the display screen 404 may be generated in the same color as the color of a portion of the glaucoma medication bottle since the glaucoma medication is most often distinguished by the color of the cap. For example, prostaglandins have a turquoise or blue cap; beta blockers have a yellow cap; alpha agonists have a purple cap or white cap; acetylcholine agonists have a green cap; and carbonic anhydrase inhibitors have an orange cap, and during a reminder portions the display screen 404 may be generated in the same color as the color of the cap of the glaucoma medication bottle associated with the compliance event. Both the picture of the box as well as the bottle serve as confirmation of the medication prescribed by the physician 101B. Most patients 101A are not aware of the specific type of medication used. By this confirmation process, the patient 101A may then be aware of how many times a day they are supposed to be taking that specific medication. This displayed information serves to provide visual confirmation to the patient 101A of the appearance of the prescribed medication associated with the compliance event and reminder. In conjunction with a voice reminder 515 (FIG. 5), the patient 101B may be shown exactly the color and name of the medication to be taken.

Referring now to FIGS. 8-16, screen shots of example blind spots 110 shaped as glaucoma associated scotomas are shown obscuring portions of the display screen I/O interface 404 of a client device 400. The blind spots 110 may be of any shape, opacity, and/or size, but preferably may be configured in the shapes of any known type of scotoma including to be discovered types of scotomas. A blind spot 110 may also be of any color of combination of colors, including white and/or black. Pixels of the display screen 404 devoted to forming a blind spot 110 effectively reduce the amount of information which would be shown on the display screen. In preferred embodiments, the size, opacity, and/or shape of the blind spots 110 may increase as the patient 101A using the client device 400 performs non-compliant actions and/or fails to perform compliant actions of medication regimen adherence.

In some embodiments, the system 100 may produce one or more blind spots 110 in the general shape of one or more glaucoma associated scotomas for gamblification or gamification. Gamblification may refer to using blind spots 110 to promote medication adherence via a client device 400 in which the blind spots 110 may be shaped as glaucoma associated scotomas which obscure portions of a game of chance or gambling type of program or application from being observed on the display screen 404A of the client device 400. The gamblification examples of FIGS. 8-16 depict a roulette type of gambling and wagering game being played on a client device 400 with portions of the gambling game (e.g. portions of the roulette table) obscured by one or more blind spots 110. In other embodiments, one or more blind spots 110 may be produced on the display screen 404 of the client device 400 to obscure portions of novelty or entertainment games being played on the client device 400 such as first person shooter games, puzzle games, skill based games, or any other type of game playable on a client device 400 as gamification. Gamification may refer to using blind spots 110 to promote medication adherence via a client device 400 in which the blind spots 110 may be shaped as glaucoma associated scotomas which obscure portions of a novelty or entertainment game type of program or application from being observed on the display screen 404A of the client device 400. Gamification is the use of game elements and game design techniques in a non-game context. Game elements are not the game itself, but the use of points, quests, avatars, resource collection, progression, social graph, and levels. In further embodiments, one or more blind spots 110 may be produced on the display screen 404 of the client device 400 to obscure portions of any information which may be displayed on a client device 400, such as weather applications, news applications, audio and video viewing applications, word processing applications, email and other messaging applications, and the like. The system 100 is not limited to the types of information that a blind spot 110 may obscure.

Figure 8:
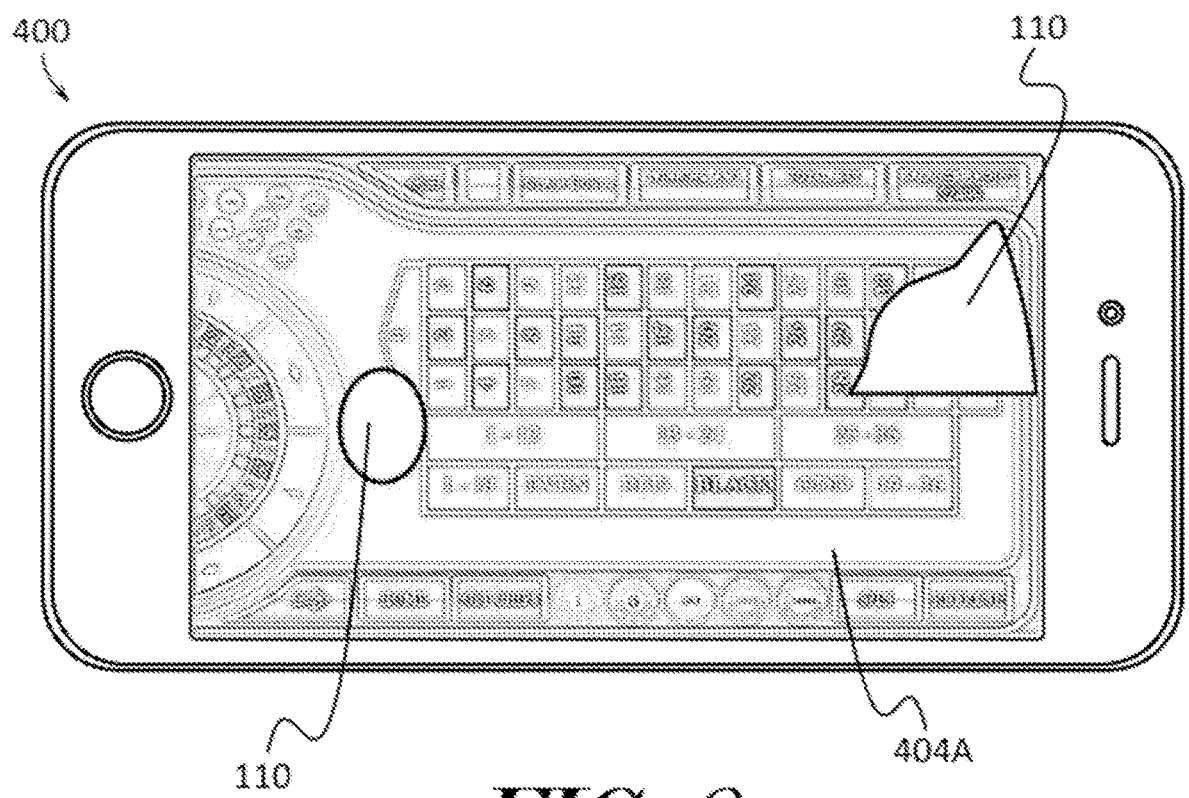
FIG. 8 illustrates a screen shot of an example of gamblification or gamification for depicting a blind spot shaped as a nasal step type glaucoma associated scotoma displayed to a user of a client device according to various embodiments described herein.
Figure 9:
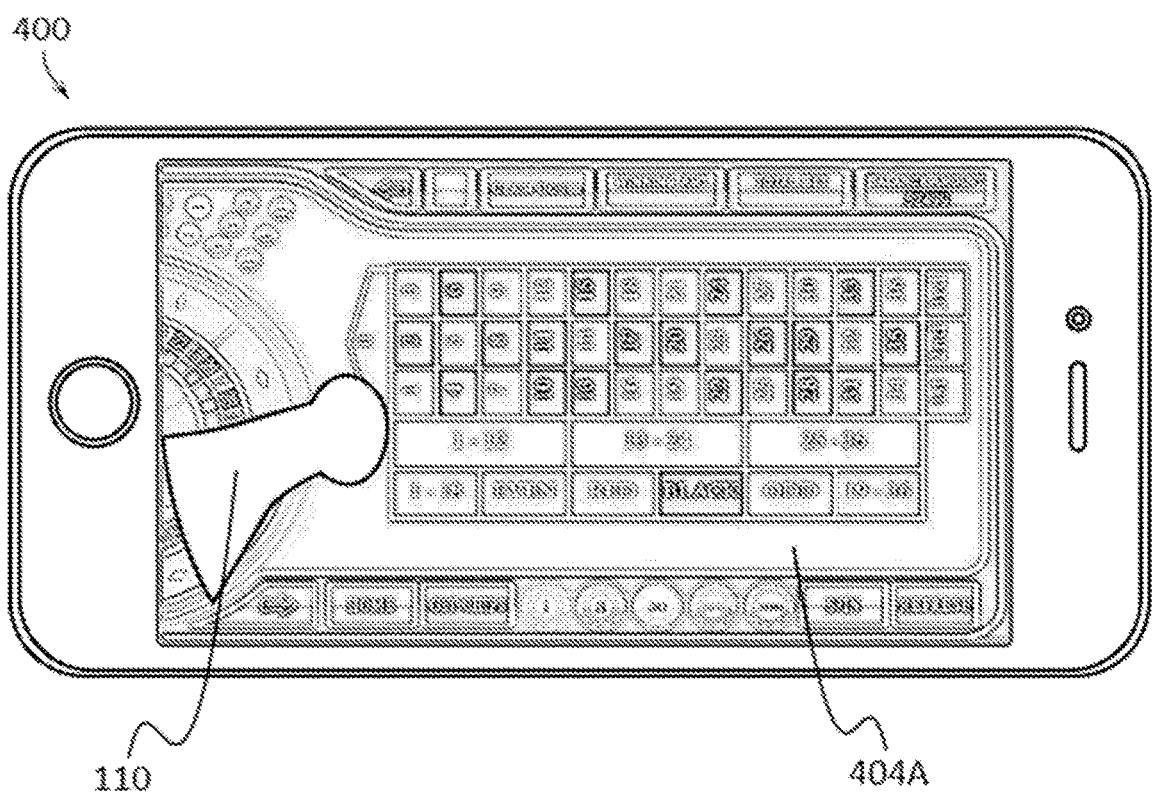
FIG. 9 shows a screen shot of an example of gamblification or gamification for depicting a blind spot shaped as a temporal wedge type glaucoma associated scotoma displayed to a user of a client device according to various embodiments described herein.
Figure 10:
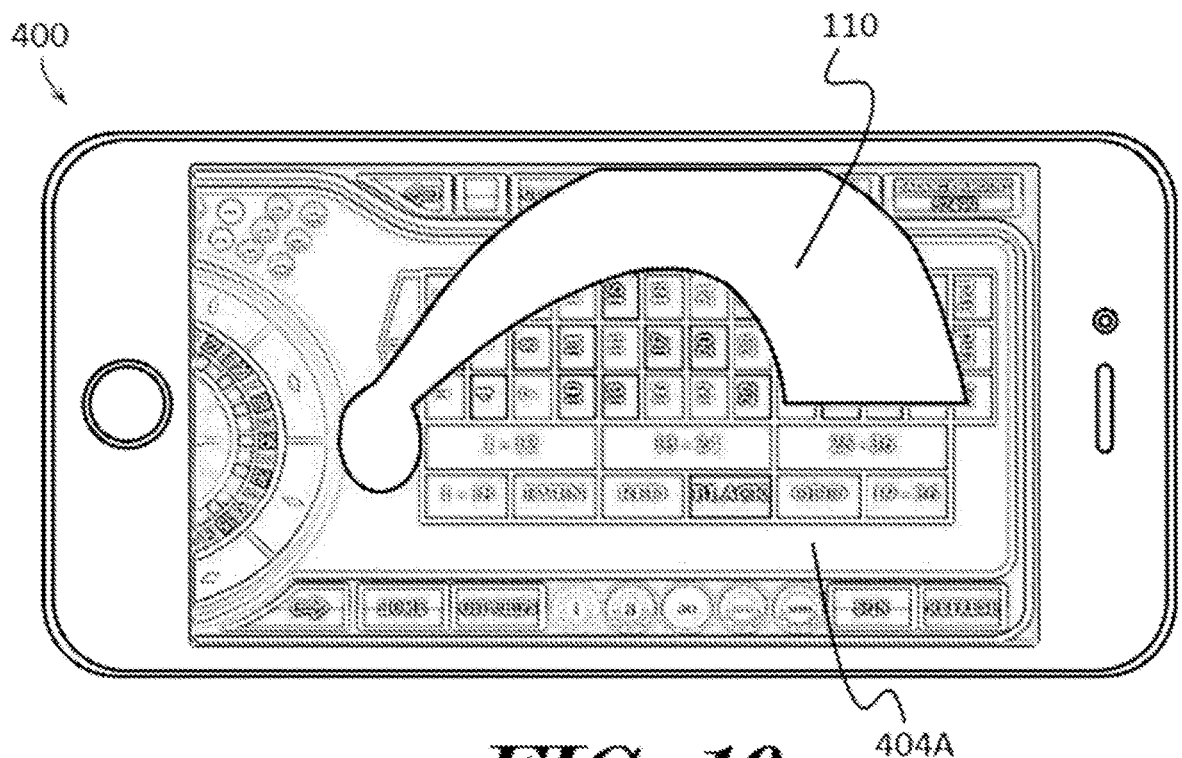
FIG. 10 depicts a screen shot of an example of gamblification or gamification for depicting a blind spot shaped as an established superior arcuate defect type glaucoma associated scotoma displayed to a user of a client device according to various embodiments described herein.
Figure 11:
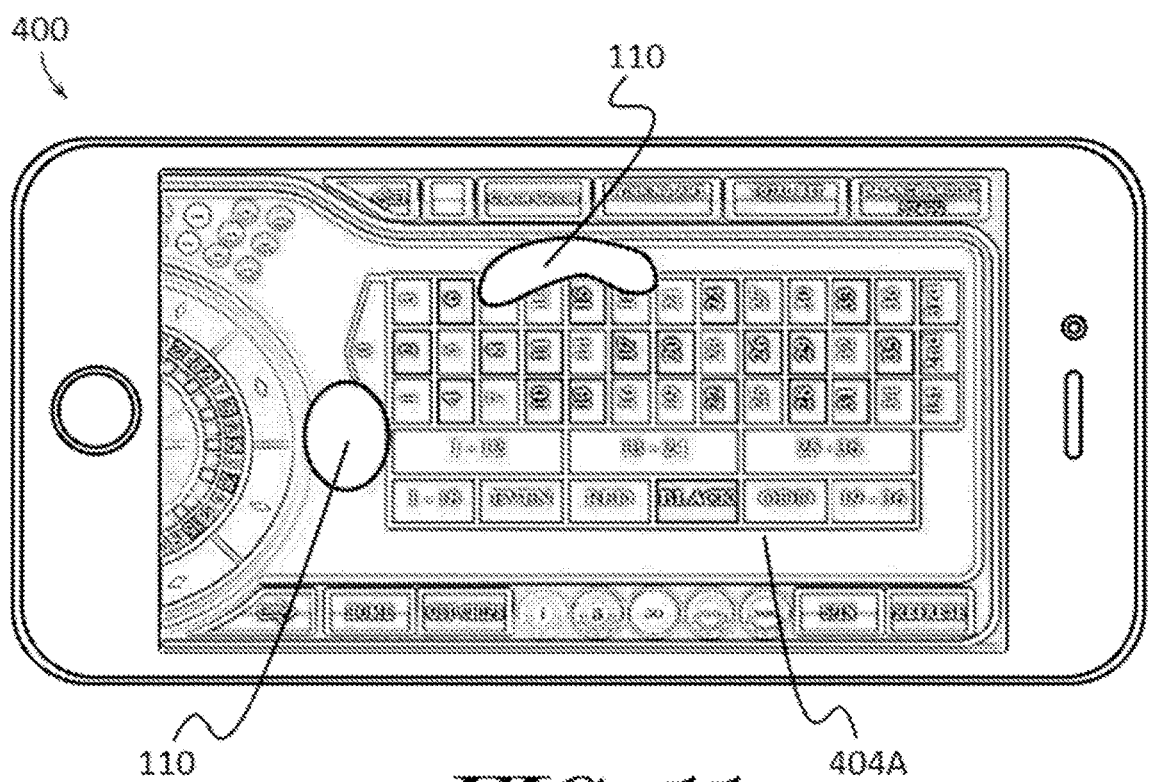
FIG. 11 illustrates a screen shot of an example of gamblification or gamification for depicting a blind spot shaped as an early superior paracentral defect at ten degrees type glaucoma associated scotoma displayed to a user of a client device according to various embodiments described herein.
Figure 12:
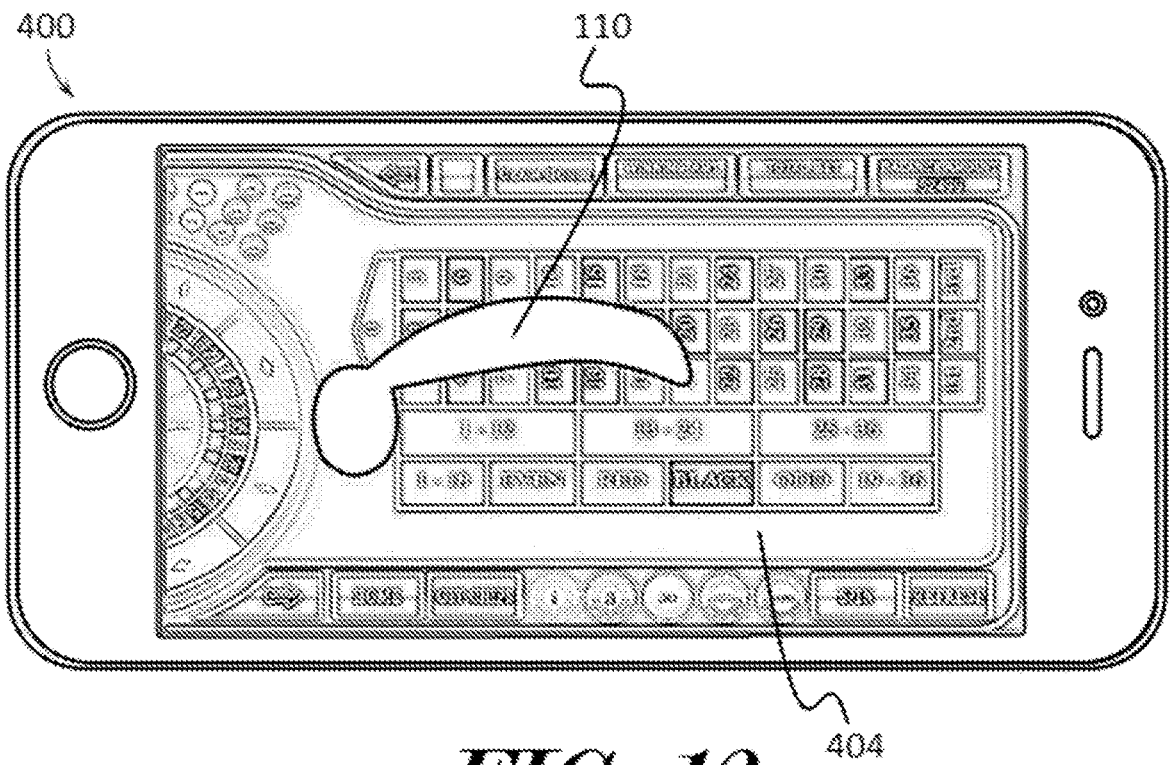
FIG. 12 shows a screen shot of an example of gamblification or gamification for depicting a blind spot shaped as a superior, fixation threatening paracentral defect type glaucoma associated scotoma displayed to a user of a client device according to various embodiments described herein.
Figure 13:
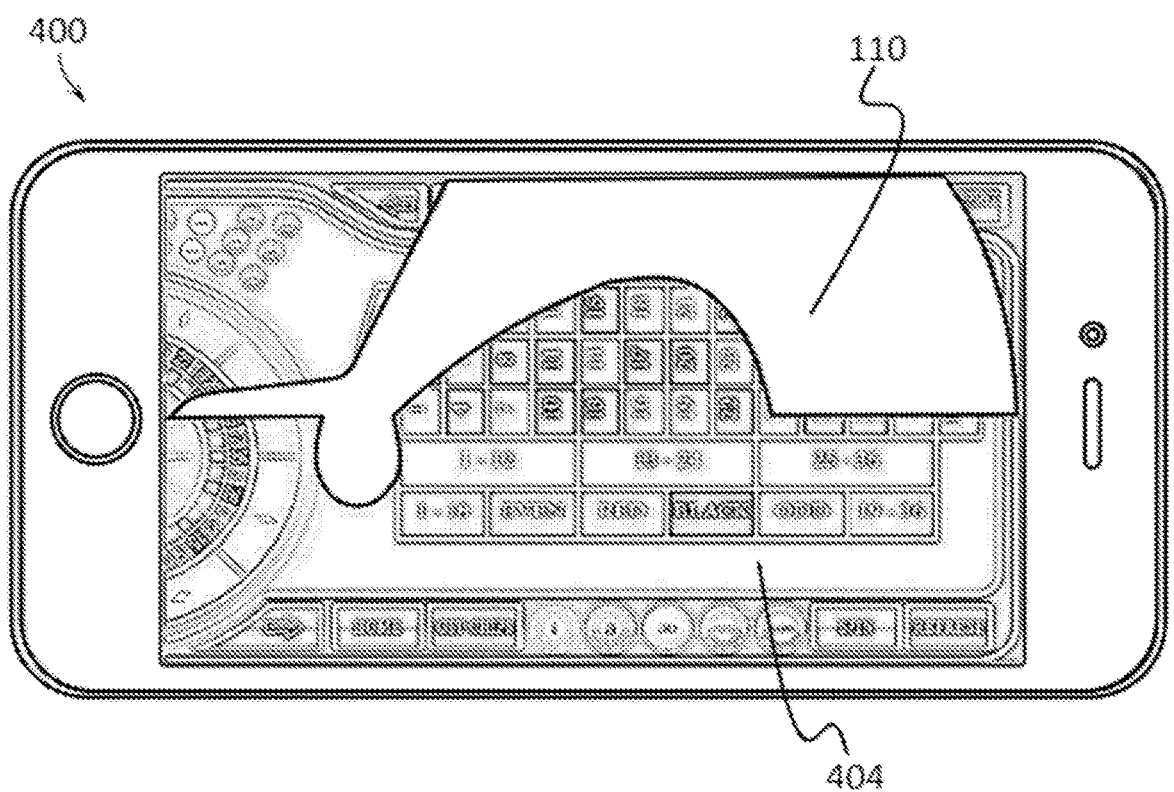
FIG. 13 depicts a screen shot of an example of gamblification or gamification for depicting a blind spot shaped as a superior arcuate with peripheral breakthrough and a blind spot shaped as early inferior defect type glaucoma associated scotoma displayed to a user of a client device according to various embodiments described herein.
Figure 14:
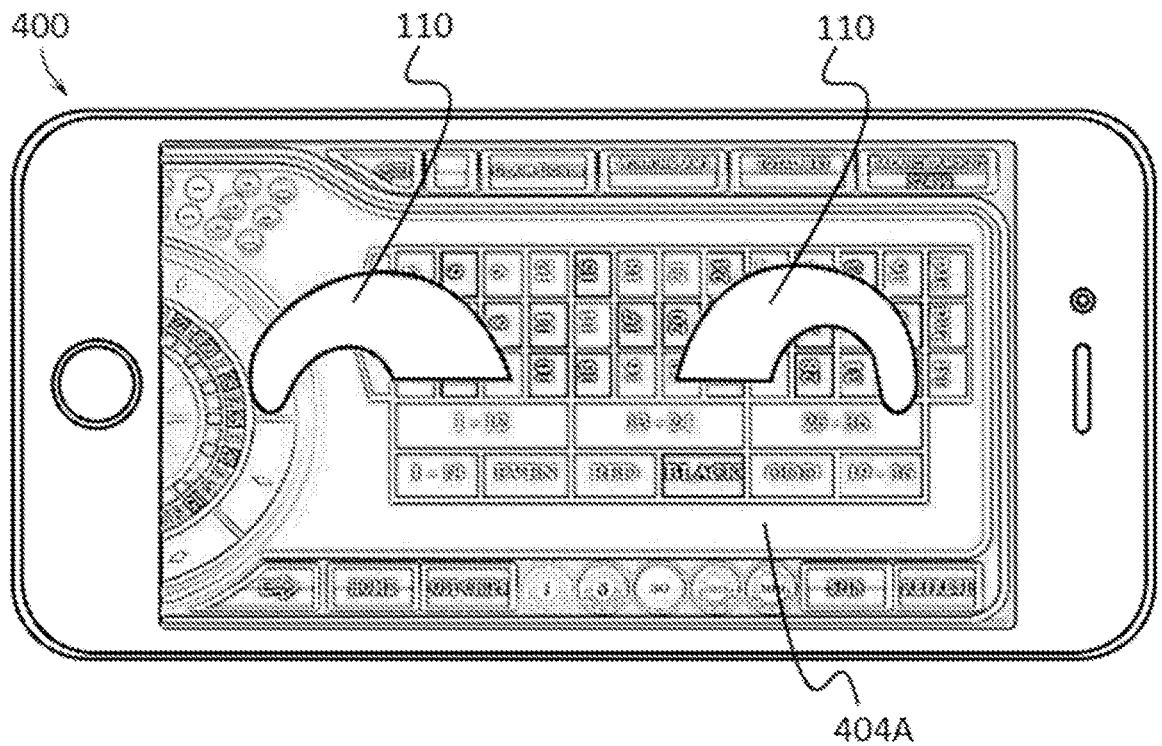
FIG. 14 illustrates a screen shot of an example of gamblification or gamification for depicting a blind spot shaped as a Bjerrum arcuate type glaucoma associated scotoma displayed to a user of a client device according to various embodiments described herein.
Figure 15:
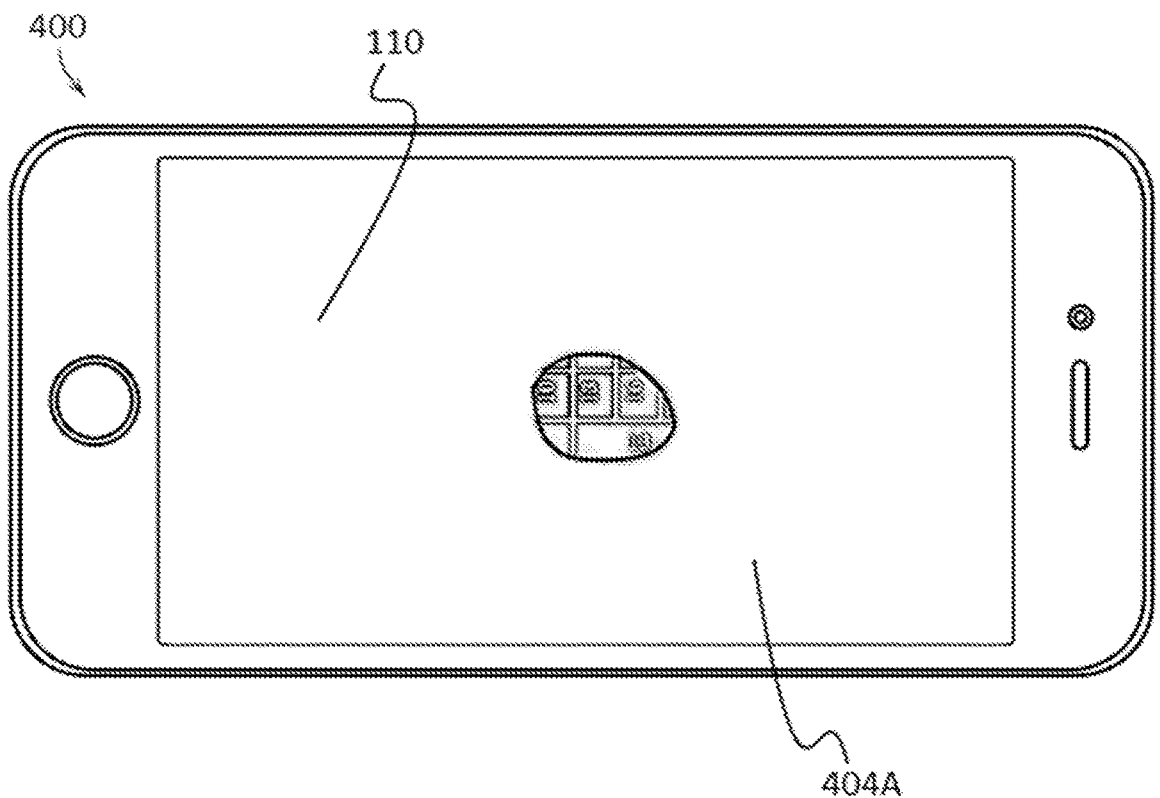
FIG. 15 shows a screen shot of an example of gamblification or gamification for depicting a blind spot shaped as a tunnel vision defect with temporal cresent sparing type glaucoma associated scotoma displayed to a user of a client device according to various embodiments described herein.
Figure 16:
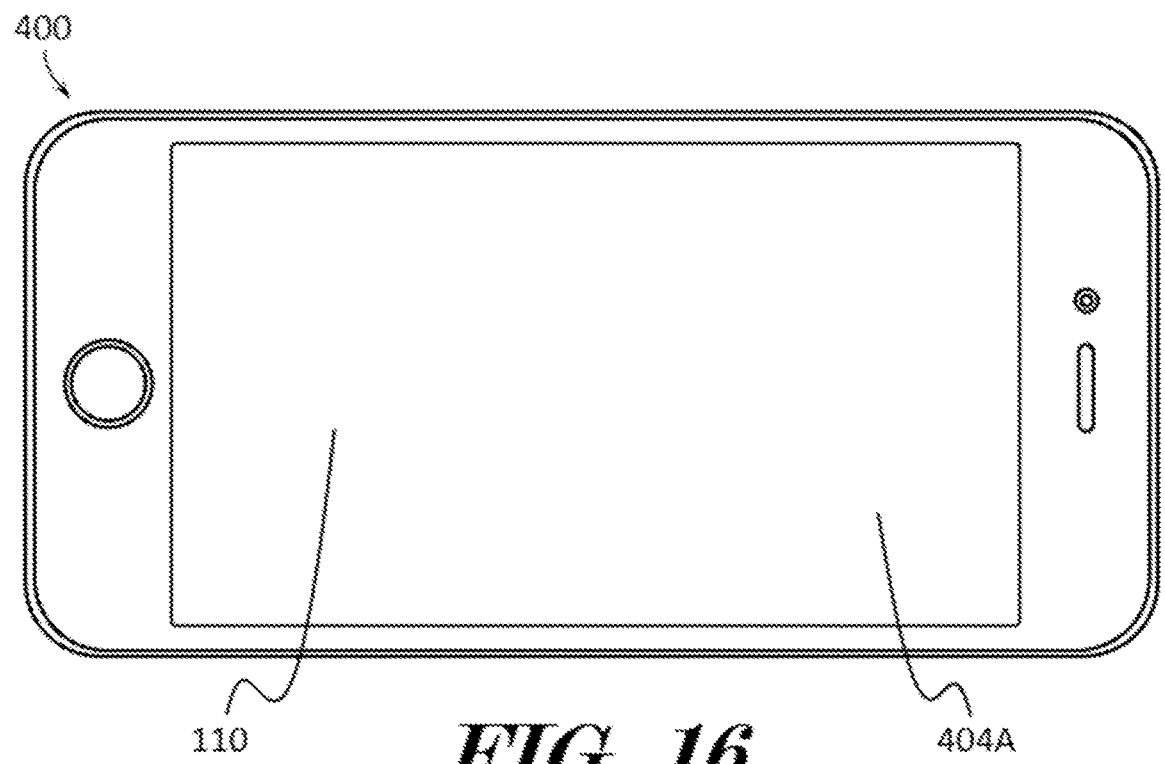
FIG. 16 depicts a screen shot of an example of gamblification or gamification for depicting a blind spot shaped as end stage complete field loss type glaucoma associated scotoma displayed to a user of a client device according to various embodiments described herein.
Figure 17:
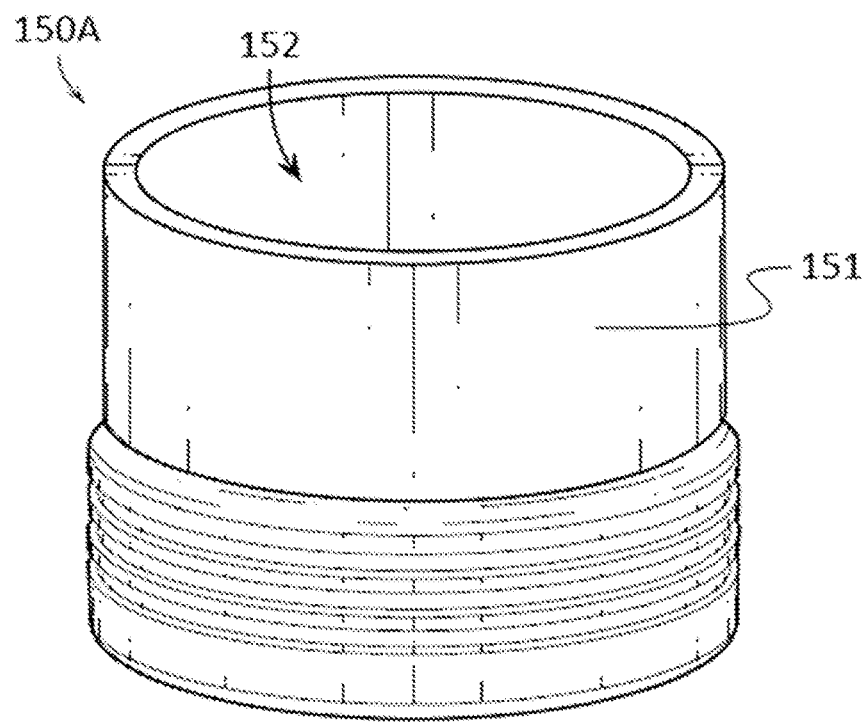
FIG. 17 illustrates a perspective view of an example of a unibody of an exemplary medication adherence device according to various embodiments described herein.

FIG. 8 illustrates a screen shot of an example of gamblification or gamification for depicting a blind spot 110 shaped as a nasal step type scotoma displayed on the display screen 404A to a user of a client device 400. FIG. 9 shows a screen shot of an example of gamblification or gamification for depicting a blind spot 110 shaped as a temporal wedge type scotoma displayed on the display screen 404A to a user of a client device 400. FIG. 10 depicts a screen shot of an example of gamblification or gamification for depicting a blind spot 110 shaped as an established superior arcuate defect type scotoma displayed on the display screen 404A to a user of a client device 400. FIG. 11 illustrates a screen shot of an example of gamblification or gamification for depicting a blind spot 110 shaped as an early superior paracentral defect at ten degrees type scotoma displayed on the display screen 404A to a user of a client device 400. FIG. 12 shows a screen shot of an example of gamblification or gamification for depicting a blind spot 110 shaped as a superior, fixation threatening paracentral defect type scotoma displayed on the display screen 404A to a user of a client device 400. FIG. 13 depicts a screen shot of an example of gamblification or gamification for depicting a blind spot 110 shaped as a superior arcuate with peripheral breakthrough and a blind spot 110 shaped as early inferior defect type scotoma displayed on the display screen 404A to a user of a client device 400. FIG. 14 illustrates a screen shot of an example of gamblification or gamification for depicting a blind spot 110 shaped as a Bjerrum arcuate type scotoma displayed on the display screen 404A to a user of a client device 400. FIG. 15 shows a screen shot of an example of gamblification or gamification for depicting a blind spot 110 shaped as a tunnel vision defect with temporal crescent sparing type scotoma displayed on the display screen 404A to a user of a client device 400. FIG. 16 depicts a screen shot of an example of gamblification or gamification for depicting a blind spot 110 shaped as end stage complete field loss in which substantially the entire display screen 404 is obstructed by a scotoma displayed on the display screen 404A to a user of a client device 400.

Figure 21:
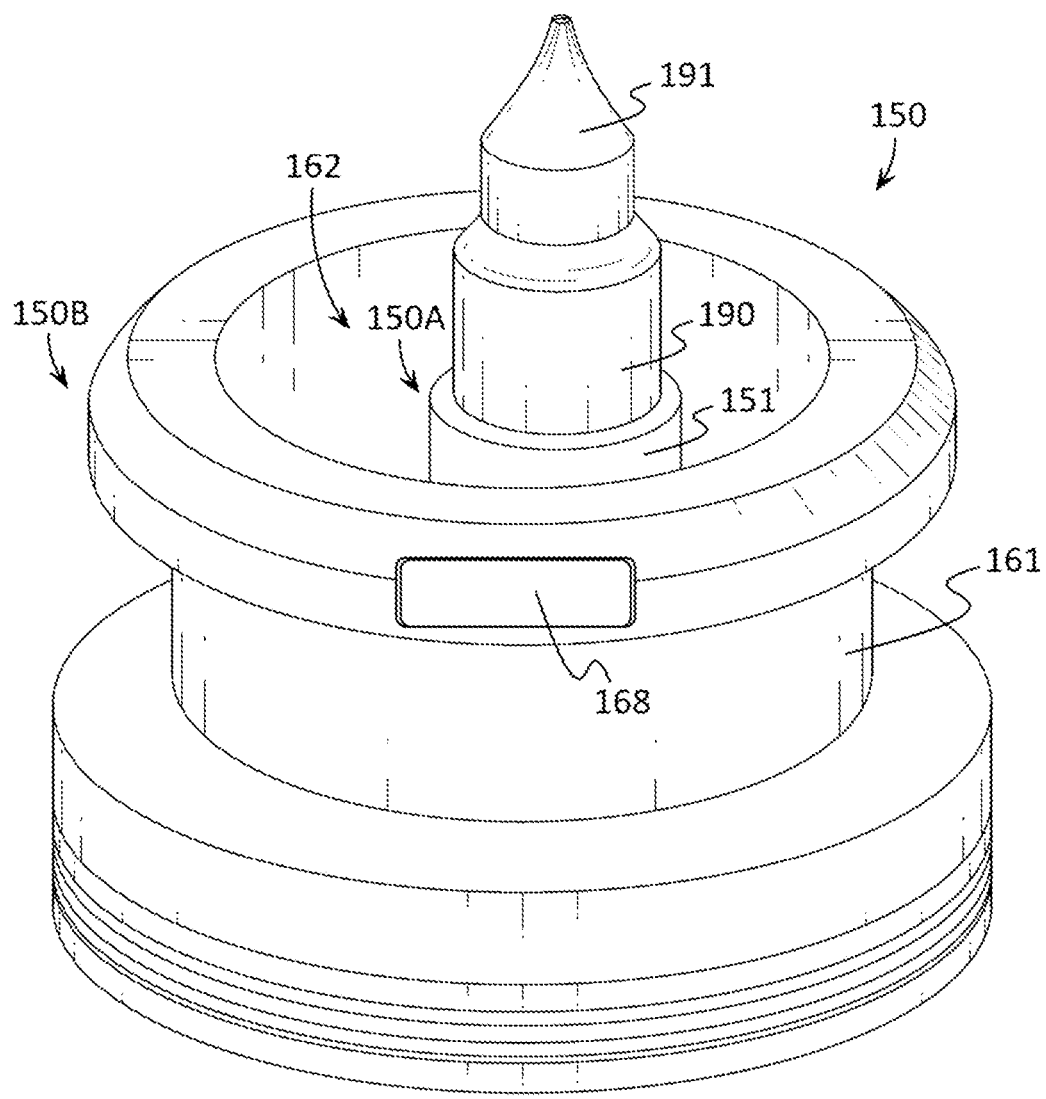
FIG. 21 shows a perspective view of an example of an exemplary medication adherence device with a unibody coupled to a lower portion of a medicine container and the unibody and medicine container received by a station according to various embodiments described herein
Figure 22:
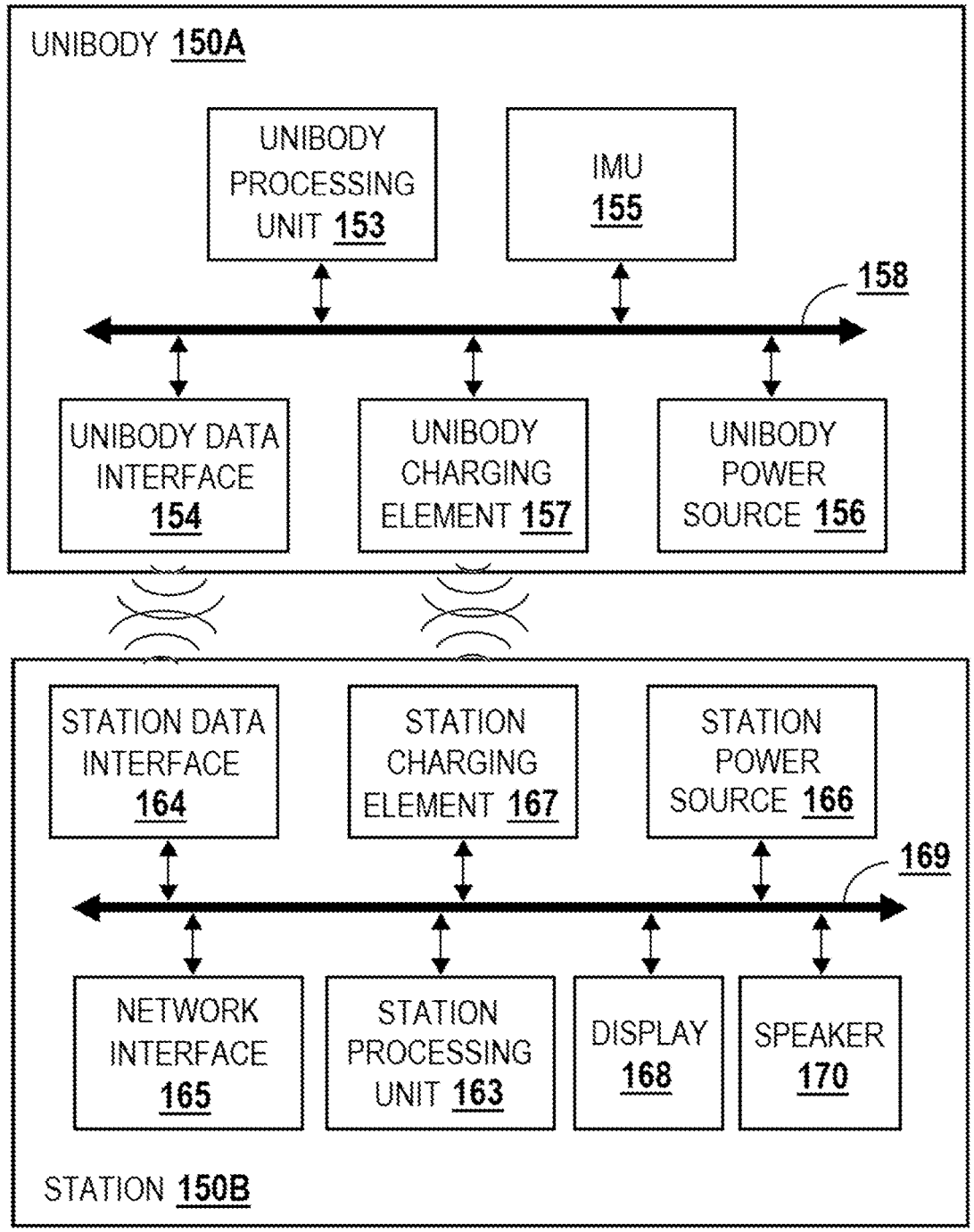
FIG. 22 depicts a block diagram of an example of a medication adherence device according to various embodiments described herein.
Figure 23:
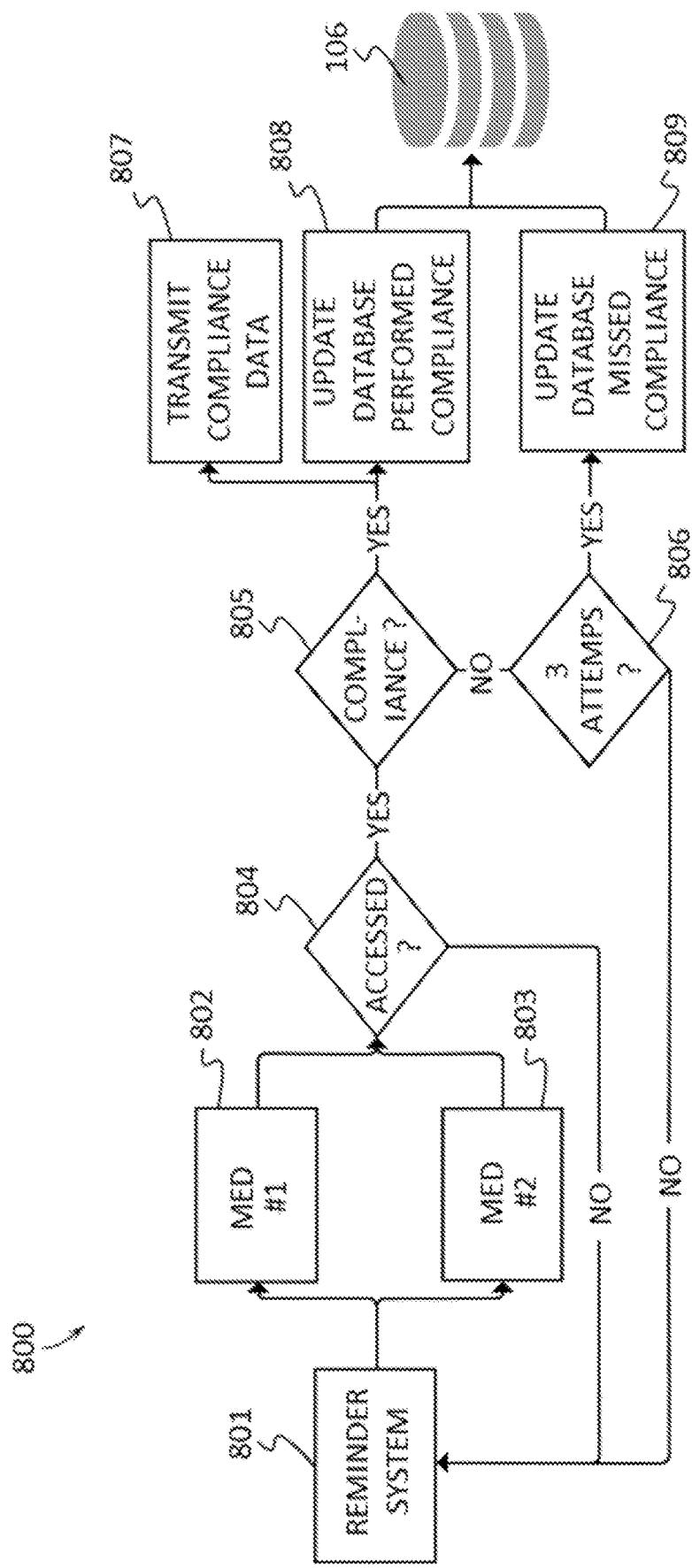
FIG. 23 illustrates a block diagram of an example of a method of promoting medication adherence via medication access information received from a medication adherence device according to various embodiments described herein.

FIGS. 21 and 22 illustrate an example of a medication adherence device ("the device") 150 according to various embodiments described herein. In some embodiments, the system 100 may receive medication access information from a device 150, and the medication access information may be used to determine if a first user or patient 101A has missed a compliance event. The device 150 may be used with any type of medicine container 190 and preferably used with a medicine container 190 for dispensing eye drop type medications having an eye dropper type of medicine container top. In some embodiments, a device 150 may comprise a unibody 150A and a station 150B. A unibody 150A may be configured to be coupled to a medicine container 190, and the station 150B may be configured to removably receive the unibody 150A. Preferably, a unibody 150A may be removably coupled to the bottom of a medicine container 190 and may be configured to detect various motions or actions that a patient 101A or other individual may perform with the medicine container 190, such as opening and closing activity of the medicine container 190, dispensing medication from the medicine container 190, and other compliance actions that may be performed by a patient 101A or other individual. By detecting, via the unibody 150A, various motions or actions that a patient 101A or other individual may perform with the medicine container 190, the device 150 may detect compliance of the patient 101A or other individual to use or to take the medicine within the medicine container 190.

In some embodiments, the unibody 150A may comprise a unibody housing 151 which may contain one or more other elements of the unibody 150A. The unibody housing 151 may be configured to be removably coupled to portions of a medicine container 190. Preferably, the unibody housing 151 may comprise a unibody cavity 152 which may be shaped to receive portions of a medicine container 190, such as lower portions of a medicine container 190. In some embodiments, the unibody cavity 152 may be generally cylindrical in shape although a unibody cavity 152 may be configured in any size and shape.

A unibody housing 151 may be made from or may comprise substantially rigid materials, such as metal and metal alloys, hard plastics, including polyethylene (PE), Ultra-high-molecular-weight polyethylene (UHMWPE, UHMW), polypropylene (PP) and polyvinyl chloride (PVC), polycarbonate, nylon, hard rubbers, wood, other plant based materials; cushioning materials, such as silicone foams, rubber foams, urethane foams including plastic foams, neoprene foam, latex foam rubber, polyurethane foam rubber, or elastomer materials such as elastic plastics, elastic silicone, elastic rubbers; and/or any other material including combinations of materials.

In some embodiments, lower portions of a medicine container 190 may be removably coupled to the unibody 150A by inserting the lower portions of a medicine container 190 into the unibody cavity 152 where it may be frictionally retained, although any other coupling method may be used. In other embodiments, a medicine container 190 may be removably coupled to the unibody 150A with any suitable removable coupling method which preferably enables lower portions of the medicine container 190 to be received into the unibody cavity 152.

In some embodiments, the unibody 150A may be a digital device that, in terms of hardware architecture may comprise a unibody processing unit 153, a unibody data interface 154, an inertial measurement unit (IMU) 155, a unibody power source 156, and a unibody charging element 157. It should be appreciated by those of ordinary skill in the art that FIG. 22 depicts the unibody 150A in an oversimplified manner, and a practical embodiment may include additional components or elements and suitably configured processing logic to support known or conventional operating features that are not described in detail herein.

The unibody processing unit 153 is a hardware device for executing software instructions. The processing unit 153 can be any custom made or commercially available processor, a central processing unit (CPU), an auxiliary processor among several processors associated with the processing unit 153, a semiconductor-based microprocessor (in the form of a microchip or chip set), a microcontroller (a small computer on a single metal-oxide-semiconductor integrated circuit chip), or generally any device for executing software instructions. The processing unit 153 may be in communication with a unibody data interface 154, an inertial measurement unit (IMU) 155, a unibody power source 156, a unibody charging element 157, and/or any other electrical element of the unibody 150A via a local interface 158. The local interface 158 may be, for example but not limited to, one or more buses or other wired or wireless connections, as is known in the art. Preferably, the unibody processing unit 153 may be configured to communicate motion data from the inertial measurement unit 155 to the unibody data interface 154. Optionally, the inertial measurement unit 155 may be configured to communicate motion data directly to the unibody data interface 154.

A unibody data interface 154 may comprise any suitable interface for sending and/or receiving data. Generally, a unibody data interface 154 may be configured to provide data recorded by an IMU 155 and/or data generated by the unibody processing unit 153 to a station 150B. In some embodiments, a unibody data interface 154 may comprise a wireless data interface which may be configured to wirelessly send and/or receive data with a station data interface 164. In preferred embodiments, a unibody data interface 154 may comprise a read/write Radio Frequency Identification (RFID) Tag. In further embodiments, a unibody data interface 154 may comprise a wireless data interface configured to operate using wireless communication protocols, such as a near field communications (NFC), Bluetooth, Wifi, or any other wireless communication protocol. In other embodiments, a unibody data interface 154 may comprise a wired data interface which may be mated with a wired station data interface 164.

In some embodiments, the unibody 150A may comprise an inertial measurement unit (IMU) 155 which may provide medication access information describing movement of the unibody 150A, and therefore, the movement of a medicine container 190 that the unibody 150A is coupled to. An IMU 155 is an electronic device that measures and reports a body's specific force, angular rate, and sometimes the magnetic field surrounding the body, using a combination of accelerometers and gyroscopes, sometimes also magnetometers. An IMU 155 works by detecting linear acceleration using one or more accelerometers and rotational rate using one or more gyroscopes, preferably as 6-axis. Some also include a magnetometer which is commonly used as a heading reference. Typical configurations contain one accelerometer, gyro, and magnetometer per axis for each of the three vehicle axes: pitch, roll and yaw. An IMU 155 may be configured to communicate position data, orientation data, position change data, and/or orientation change data about the unibody 150A to a processing unit 153. This data may be used by the processing unit 153 to determine if and when a medication in the medicine container 190 was administered to an individual, such as the patient 101A associated with the medicine container 190. In preferred embodiments, an IMU 155 may provide data to the processing unit 153 which describes inversion, twisting, and/or turning motions of the unibody 150A, and a medicine container 190 coupled thereto, and this data may be used by the processing unit 153 to determine if the medicine is being taken or administered to the patient 101A associated with the medicine container 190.

In some embodiments, an IMU 155 may comprise a micro electro-mechanical system (MEMS) gyroscope. In other embodiments, an IMU 155 may comprise a fiber optic gyroscope (FOG) gyroscope, a hemispherical resonator gyroscope (HRG), a vibrating structure gyroscope (VSG) or a Coriolis Vibratory Gyroscope (CVG), a dynamically tuned gyroscope (DTG), a ring laser gyroscope (RLG), a London moment gyroscope, a tilt sensor such as a MEMS tilt sensor, any other type of tilt sensor, or any other suitable device that is able to measure and electrically communicate tilt data, positional data, and/or orientation data. In further embodiments, an IMU 155 may comprise any type of accelerometer including capacitive accelerometers, piezoelectric accelerometers, piezo-resistive accelerometers, hall effect accelerometers, magneto resistive accelerometers, heat transfer accelerometers, micro-electro mechanical system (MEMS) accelerometers, NANO technology accelerometers, or any other suitable device that is able to measure acceleration and to electrically communicate acceleration data.

In some embodiments, the unibody 150A may comprise a unibody power source 156 which may provide electrical power to any component that may require electrical power. A power source 156 may comprise a battery, and more preferably a rechargeable battery, such as a lithium ion battery, nickel cadmium battery, alkaline battery, or any other suitable type of battery, a fuel cell, a capacitor, a super capacitor, or any other type of energy storing and/or electricity releasing device. In further embodiments, a power source 156 may be in communication with a unibody charging element 157 that may be configured to supply electrical power to the power source 156. In preferred embodiments, a unibody charging element 157 may comprise an inductive charging or wireless power receiver or coil. In further embodiments, a unibody charging element 157 may comprise a power cord, kinetic or piezo electric battery charging device, a solar cell or photovoltaic cell, etc. In further embodiments, a unibody charging element 157 may comprise a power charging and distribution module which may be configured to control the recharging of the power source 156, discharging of the power source 156, and/or distribution of power to one or more components of the unibody 150A that may require electrical power.

The device 150 may comprise a station 150B which may be configured to receive data describing the motion (or lack thereof) of a unibody 150A, and therefore data describing the motion (or lack thereof) of a medicine container 190 that the unibody 150A is removably coupled to.

The station 150B may comprise a station housing 161 which may contain one or more other elements of the station 150B. In some embodiments, the station housing 161 may be configured to receive, support, or otherwise contact a unibody 150A. Preferably, the station housing 161 may comprise a station cavity 162 which may be shaped to receive portions of a unibody 150A that may be coupled to a medicine container 190 as shown in FIG. 21. In some embodiments, the station cavity 162 may be generally cylindrical in shape, although a station cavity 162 may be configured in any shape and size.

A station housing 161 may be made from or may comprise substantially rigid materials, such as metal and metal alloys, hard plastics, including polyethylene (PE), Ultra-high-molecular-weight polyethylene (UHMWPE, UHMW), polypropylene (PP) and polyvinyl chloride (PVC), polycarbonate, nylon, hard rubbers, wood, other plant based materials; cushioning materials, such as silicone foams, rubber foams, urethane foams including plastic foams, neoprene foam, latex foam rubber, polyurethane foam rubber, or elastomer materials such as elastic plastics, elastic silicone, elastic rubbers; and/or any other material including combinations of materials.

In some embodiments, the station 150B may be a digital device that, in terms of hardware architecture may comprise a station processing unit 163, a station data interface 164, a network interface 165, a station power source 166, and a station charging element 167. It should be appreciated by those of ordinary skill in the art that FIG. 22 depicts the station 150B in an oversimplified manner, and a practical embodiment may include additional components or elements and suitably configured processing logic to support known or conventional operating features that are not described in detail herein.

The station processing unit 163 is a hardware device for executing software instructions. The processing unit 163 can be any custom made or commercially available processor, a central processing unit (CPU), an auxiliary processor among several processors associated with the processing unit 163, a semiconductor-based microprocessor (in the form of a microchip or chip set), a microcontroller (a small computer on a single metal-oxide-semiconductor integrated circuit chip), or generally any device for executing software instructions. The processing unit 163 may be in communication with a station data interface 164, a network interface 165, a station power source 166, a station charging element 167, and/or any other electrical element of the station 150B via a local interface 169. The local interface 169 may be, for example but not limited to, one or more buses or other wired or wireless connections, as is known in the art.

A station data interface 164 may comprise any suitable interface for sending and/or receiving data. Generally, a station data interface 164 may be configured to send and/or receive data with a unibody data interface 154 of a unibody 150A. In some embodiments, a station data interface 164 may comprise a wireless data interface which may be configured to wirelessly send and/or receive data with a unibody data interface 154. In preferred embodiments, a station data interface 164 may comprise a read/write Radio Frequency Identification (RFID) Tag Reader/Writer. In further embodiments, a station data interface 164 may comprise a wireless data interface configured to operate using wireless communication protocols, such as a near field communications (NFC), Bluetooth, Wifi, or any other wireless communication protocol. In other embodiments, a station data interface 164 may comprise a wired data interface which may be mated with a wired unibody data interface 154.

A network interface 165 enables data communication with an external access client device 400, server 300, or network 105. Generally, a station data interface 164 may be configured to provide data, such medication access information generated by a unibody 150A and/or station 150B to a network 105, and more preferably to a client device 400 and/or server 300 via a network 105. In preferred embodiments, a station data interface 164 may be or comprise a wireless network interface that may support any number of suitable wireless data communication protocols, techniques, or methodologies can be supported by the network interface 165, including, without limitation: cellular/wireless/cordless telecommunication protocols (e.g. 3G/4G/5G, etc.); RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; Long Term Evolution (LTE); wireless home network communication protocols; paging network protocols; magnetic induction; satellite data communication protocols; wireless hospital or health care facility network protocols such as those operating in the WMTS bands; GPRS; proprietary wireless data communication protocols such as variants of Wireless USB; and any other protocols for wireless communication. In other embodiments, a station data interface 164 may be or comprise a wired network interface, such as an ethernet network interface.

In some embodiments, a station 150B may comprise a station power source 166 which may provide electrical power to any component that may require electrical power. A power source 166 may comprise a battery, and more preferably a rechargeable battery, such as a lithium ion battery, nickel cadmium battery, alkaline battery, or any other suitable type of battery, a fuel cell, a capacitor, a super capacitor, or any other type of energy storing and/or electricity releasing device. In further embodiments, a power source 166 may be in communication with a station charging element 167 that may be configured to supply electrical power to the power source 166 and/or configured to supply electrical power to the unibody charging element 157. In preferred embodiments, a station charging element 167 may comprise an inductive charging or wireless power receiver or coil that may be used to supply power to a unibody power source 156 via a unibody charging element 157 of a unibody 150A that may be positioned in the station cavity 162 or otherwise proximate to the station 150B. In this manner, a station charging element 167 may communicate power to a unibody charging element 157 via inductive charging. In further embodiments, a station charging element 167 may comprise a power cord, kinetic or piezo electric battery charging device, a solar cell or photovoltaic cell, etc. In further embodiments, a station charging element 167 may comprise a power charging and distribution module which may be configured to control the recharging of the power source 166, discharging of the power source 166, and/or distribution of power to one or more components of the station 150B that may require electrical power.

In some embodiments, the device 150 may comprise a display 168 which may be configured to visually apprise a user 101 of the status of one or more elements of the device 150 and/or of one or more conditions that the device 150 is in. For example, if all elements of the device 150 are working properly, a light emitting type of display 168, such as a LED light, may be operated by the station processing unit 163 to emit green light. As another example, an display 168 may be configured to visually apprise a user 101 of the status or charge level of a power source 156, 166. In some embodiments, a display 168 may be configured as a light emitting element which may be used to provide visual reminders to a patient 101A. In preferred embodiments, a display 168 may comprise a display screen that may be configured to provide visual information to a user and optionally to receive input from a user such as a touch screen display. In further preferred embodiments, a display 168 may be configured to visually display medication access information generated by a medication adherence device 150 or other component of the system 100. A display screen display 168 may comprise a Liquid crystal display (LCD), Light-emitting diode display (LED), Electroluminescent display (ELD), Electronic paper, E Ink, Plasma display panel (PDP), Cathode ray tube display (CRT), High-Performance Addressing display (HPA), Thin-film transistor display (TFT), Organic light-emitting diode display (OLED), Surface-conduction electron-emitter display (SED), Laser TV, Carbon nanotubes, Quantum dot display, and/or Interferometric modulator display (IMOD).

In some embodiments, the device 150 may comprise a speaker 170 which may be used to produce a plurality of sounds at a plurality of volume levels. In preferred embodiments, a station 150B may comprise a speaker 170. A speaker 170 may comprise a buzzer, a piezoelectric sound producing device, a dielectric elastomer sound producing device, a buzzer, a moving coil loudspeaker, an electrostatic loudspeaker, an isodynamic loudspeaker, a piezo-electric loudspeaker, or any other device capable of producing one or more sounds.

A device 150 may comprise one or more processing units 153, 163, which may be configured to process data from an IMU 155 of a unibody 150A. In some embodiments, intermediate processing of the data from the IMU 155 may be done by the unibody processing unit 153, and the processed data may then be communicated to the station processing unit 163 via the data interfaces 154, 164. For example, roll, pitch, yaw, and acceleration motion data output from the IMU 155 may be an analog output, and a unibody processing unit 153 may provide intermediate processing by acting as an analog-digital (A/D) convertor to convert the data so that an RFID tag type unibody data interface 154 can interface with it. This data may then be post-processed by the station processing unit 163 to get the medical adherence data (including statistics, adherence score etc.).

In preferred embodiments, the orientation of a medicine container 190 coupled to the unibody 150A may be precisely monitored by the IMU 155. When a patient 101A or caregiver picks up the unibody 150A with medicine container 190, opens the cap 191 and tilts the medicine container 190, an accelerometer coupled with a gyroscope in the IMU 155 records the motion as motion data. Optionally, the motion data is used by the IMU 155 and/or processing unit 153 as medication access information which may be used to determine if a user 101 has missed and/or performed one or more compliance events if a certain combination of acceleration and orientation/angular velocity is achieved. The intermediate processing of the data from the IMU 155 may be done by the unibody processing unit 153, and the data may be parallelly transferred onto a unibody data interface 154 that comprises a Radio Frequency Identification (RFID) tag, so that when the unibody 150A is positioned onto the station 150B, the RFID tag unibody data interface 154 transmits the post-processed data onto the station data interface 164 comprising a RFID reader, or otherwise once they are in range. Once the unibody 150A is placed onto the station 150B, or when the data from the unibody 150A is communicated to the station 150B, the data from the RFID reader station data interface 164 is finally post-processed using the station processing unit 163 to generate the medical adherence data (including statistics, adherence score etc.). Medical adherence data may then relayed onto a LED/LCD display screen display 168. Preferably, the data to be displayed on the display 168 may be customizable and real-time. Examples of Medical adherence data that may be displayed by a display 168 and/or display screen 404A may include: Real-time Adherence Score (out of 100)—this may be updated monthly or weekly and is useful for reporting to the doctor, physicians, second user or vision care provider 101B; gamification data (Points, scores etc.); battery information; reminder for next dosage (blink, sound, etc.)

Preferably, the data may also be communicated to a server 300 of the system 100 which may access, analyze and present the data, via a network interface 165, such as which provides a 3G network service. This enables all the data generated by a device 150, such as medication access information to the system which may be used to determine if a user has missed and/or performed one or more compliance events, to be accessed across multiple client devices 400, such as the patient smartphone (for reminders), doctor's clinic computer platforms, insurance company computer platforms, etc.

FIG. 22 depicts a block diagram of an example of a method of promoting medication adherence via medication access information received from a medication adherence device ("the method") 800 according to various embodiments described herein. The method 800 may be used to determining if a first user or patient 101A has missed or performed one or more compliance events based on medication access information received from one or more medication adherence devices 150. One or more steps of the method may be performed by an incentivization application 421, a defect representation application 422, and/or a communication module 423.

In some embodiments, the method 800 may start preferably after a treatment plan for the patient 101A has been created in step 503 of the method of promoting medication adherence 500 detailed in FIG. 5. In step 801 a reminder system performed by the incentivization application 421 may provide a reminder for a daily compliance event for each medicine (in this example, a first medicine 802 and a second medicine 803, via the client device 400 of the patient 101A. Preferably, the reminder may comprise a visual reminder displayed on the display screen 404A optionally comprising a picture of the medication, an audible reminder provided by a speaker-type IO interface 404 optionally comprising a tone, a vocal message, song, or the like, and/or a tactile reminder provided by a vibration-type IO interface 404.

In step 802, the user 101A may be presented with a reminder to take a first medication that was prescribed to them by the vision care provider 101B on the client device 400 by the incentivization application 421. The first medication may be stored in a medicine container 190 that a medication adherence device 150 may be coupled to. At decision block 804, the system 100 may determine if the medication of the medicine container 190 of the first medicine was accessed, opened, dispensed, etc., via motion data recorded by an IMU 155 of the device 150. If the medicine container 190 was not accessed, the method 800 may continue to step 801 and another reminder may be provided to the patient 101A.

If the medicine container 190 was accessed, opened, dispensed, etc., the method 800 may continue to decision block 805 and the system 100 may determine if the patient 101A performed a compliance event (by taking or being administered the first medication) or if the patient 101A missed a compliance event (by not taking or not being administered the first medication). Decision block 805 may be used to prevent false performed compliance events. Preferably, the system 100 may use motion and positional data provided by the inertial measurement unit (IMU) 155 of the first device 150 for the determination. The motion data, acceleration data, and positional information provided by the IMU 155 may be used by a processor, such as a unibody processing unit 153, station processing unit 163, processor 302, processor 402, of the system 100 to differentiate between performed compliance events and missed compliance events, such as simply opening and closing (coupling and uncoupling) the device 150 from its respective medicine container 190. If the system 100 determines that the patient 101A has performed a compliance event, the method 800 may continue to step 807 in which the performed compliance data may be transmitted by a device 150 to a client device 400 and/or server 300 or transmitted by a client device 400 to a server 300, and the method 800 may also continue to step 808 in which the system database 106 may be updated or otherwise provided with the performed compliance data for the patient 101A.

If the patient 101A missed a compliance event or after 3 attempts or a number of attempts designated by the user 101A or provider 101B, the patient 101A has not used the medication, the system 100 may determine that the patient 101A has missed the compliance event and the method may proceed to step 809. In step 809, the missed compliance data may be transmitted by a device 150 to a client device 400 and/or server 300 or transmitted by a client device 400 to a server 300, and the system database 106 may be updated or otherwise provided with the missed compliance data for the patient 101A.

If the patient 101A was prescribed a second medication, the system 100 may comprise a second medication adherence device 150 that may be coupled to the medicine container 190 of the second medication. In step 803, the patient 101A may be presented with a reminder to take the second medication that was prescribed to them by the vision care provider 101B on the client device 400 by the incentivization application 421. At decision block 804, the system 100 may determine if the medication of the medicine container 190 of the second medicine was accessed, opened, dispensed, etc., via motion data recorded by an IMU 155 of the second device 150. If the medicine container 190 was not accessed, the method 800 may continue to step 801 and another reminder may be provided to the patient 101A.

If the medicine container 190 was accessed, opened, dispensed, etc., the method 800 may continue to decision block 805 and the system 100 may determine if the patient 101A performed a compliance event (by taking or being administered the second medication) or if the patient 101A missed a compliance event (by not taking or not being administered the second medication). Decision block 805 may be used to prevent false performed compliance events. Preferably, the system 100 may use motion and positional data provided by the inertial measurement unit (IMU) 155 of the second device 150 for the determination. The motion data, acceleration data, and positional information provided by the IMU 155 may be used by a processor, such as a unibody processing unit 153, station processing unit 163, processor 302, processor 402, of the system 100 to differentiate between performed compliance events and missed compliance events. If the system 100 determines that the patient 101A has performed a compliance event, the method 800 may continue to step 807 in which the performed compliance data may be transmitted by a device 150 to a client device 400 and/or server 300 or transmitted by a client device 400 to a server 300, and the method 800 may also continue to step 808 in which the system database 106 may be updated or otherwise provided with the performed compliance data for the patient 101A.

If the patient 101A missed a compliance event, or after a number of attempts, such as three, designated by the user 101A or provider 101B, the system 100 may determine that the patient 101A has missed the compliance event and the method may proceed to step 809. In step 809, the missed compliance data may be transmitted by a client device 400 that is in communication with the device 150 to a server 300 and the system database 106 may be updated or otherwise provided with the missed compliance data for the patient 101A.

It will be appreciated that some exemplary embodiments described herein may include one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the methods and/or systems described herein. Alternatively, some or all functions may be implemented by a state machine that has no stored program instructions, or in one or more application specific integrated circuits (ASICs), in which each function or some combinations of certain of the functions are implemented as custom logic. Of course, a combination of the two approaches may be used. Moreover, some exemplary embodiments may be implemented as a computer-readable storage medium having computer readable code stored thereon for programming a computer, server, appliance, device, etc. each of which may include a processor to perform methods as described and claimed herein. Examples of such computer-readable storage mediums include, but are not limited to, a hard disk, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory), a Flash memory, and the like.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a tangible program carrier for execution by, or to control the operation of, data processing apparatus. The tangible program carrier can be a propagated signal or a computer readable medium. The propagated signal is an artificially generated signal, e.g., a machine generated electrical, optical, or electromagnetic signal that is generated to encode information for transmission to suitable receiver apparatus for execution by a computer. The computer readable medium can be a machine readable storage device, a machine readable storage substrate, a memory device, a composition of matter effecting a machine readable propagated signal, or a combination of one or more of them.

A computer program (also known as a program, software, software application, application, script, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Additionally, the logic flows and structure block diagrams described in this patent document, which describe particular methods and/or corresponding acts in support of steps and corresponding functions in support of disclosed structural means, may also be utilized to implement corresponding software structures and algorithms, and equivalents thereof. The processes and logic flows described in this specification can be performed by one or more programmable processors executing one or more computer programs to perform functions by operating on input data and generating output.

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, solid state drives, or optical disks. However, a computer need not have such devices.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network or the cloud. The relationship of client and server arises by virtue of computer programs running on the respective computers and having a client server relationship to each other.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequence of actions described herein can be considered to be embodied entirely within any form of computer readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

The computer system may also include a main memory, such as a random access memory (RAM) or other dynamic storage device (e.g., dynamic RAM (DRAM), static RAM (SRAM), and synchronous DRAM (SDRAM)), coupled to the bus for storing information and instructions to be executed by processor. In addition, the main memory may be used for storing temporary variables or other intermediate information during the execution of instructions by the processor. The computer system may further include a read only memory (ROM) or other static storage device (e.g., programmable ROM (PROM), erasable PROM (EPROM), and electrically erasable PROM (EEPROM)) coupled to the bus for storing static information and instructions for the processor.

The computer system may also include a disk controller coupled to the bus to control one or more storage devices for storing information and instructions, such as a magnetic hard disk, and a removable media drive (e.g., floppy disk drive, read-only compact disc drive, read/write compact disc drive, compact disc jukebox, tape drive, and removable magneto-optical drive). The storage devices may be added to the computer system using an appropriate device interface (e.g., small computer system interface (SCSI), integrated device electronics (IDE), enhanced-IDE (E-IDE), direct memory access (DMA), or ultra-DMA).

The computer system may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system may also include a display controller coupled to the bus to control a display, such as a cathode ray tube (CRT), liquid crystal display (LCD) or any other type of display, for displaying information to a computer user. The computer system may also include input devices, such as a keyboard and a pointing device, for interacting with a computer user and providing information to the processor. Additionally, a touch screen could be employed in conjunction with display. The pointing device, for example, may be a mouse, a trackball, or a pointing stick for communicating direction information and command selections to the processor and for controlling cursor movement on the display. In addition, a printer may provide printed listings of data stored and/or generated by the computer system.

The computer system performs a portion or all of the processing steps of the invention in response to the processor executing one or more sequences of one or more instructions contained in a memory, such as the main memory. Such instructions may be read into the main memory from another computer readable medium, such as a hard disk or a removable media drive. One or more processors in a multi-processing arrangement may also be employed to execute the sequences of instructions contained in main memory. In alternative embodiments, hard-wired circuitry may be used in place of or in combination with software instructions. Thus, embodiments are not limited to any specific combination of hardware circuitry and software.

As stated above, the computer system includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system, for driving a device or devices for implementing the invention, and for enabling the computer system to interact with a human user. Such software may include, but is not limited to, device drivers, operating systems, development tools, and applications software. Such computer readable media further includes the computer program product of the present invention for performing all or a portion (if processing is distributed) of the processing performed in implementing the invention.

The computer code or software code of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

Various forms of computer readable media may be involved in carrying out one or more sequences of one or more instructions to processor for execution. For example, the instructions may initially be carried on a magnetic disk of a remote computer. The remote computer can load the instructions for implementing all or a portion of the present invention remotely into a dynamic memory and send the instructions over the air (e.g. through a wireless cellular network or wifi network). A modem local to the computer system may receive the data over the air and use an infrared transmitter to convert the data to an infrared signal. An infrared detector coupled to the bus can receive the data carried in the infrared signal and place the data on the bus. The bus carries the data to the main memory, from which the processor retrieves and executes the instructions. The instructions received by the main memory may optionally be stored on storage device either before or after execution by processor.

The computer system also includes a communication interface coupled to the bus. The communication interface provides a two-way data communication coupling to a network link that is connected to, for example, a local area network (LAN), or to another communications network such as the Internet. For example, the communication interface may be a network interface card to attach to any packet switched LAN. As another example, the communication interface may be an asymmetrical digital subscriber line (ADSL) card, an integrated services digital network (ISDN) card or a modem to provide a data communication connection to a corresponding type of communications line. Wireless links may also be implemented. In any such implementation, the communication interface sends and receives electrical, electromagnetic or optical signals that carry digital data streams representing various types of information.

The network link typically provides data communication to the cloud through one or more networks to other data devices. For example, the network link may provide a connection to another computer or remotely located presentation device through a local network (e.g., a LAN) or through equipment operated by a service provider, which provides communication services through a communications network. In preferred embodiments, the local network and the communications network preferably use electrical, electromagnetic, or optical signals that carry digital data streams. The signals through the various networks and the signals on the network link and through the communication interface, which carry the digital data to and from the computer system, are exemplary forms of carrier waves transporting the information. The computer system can transmit and receive data, including program code, through the network(s) and, the network link and the communication interface. Moreover, the network link may provide a connection through a LAN to a client device such as a personal digital assistant (PDA), laptop computer, or cellular telephone. The LAN communications network and the other communications networks such as cellular wireless and wifi networks may use electrical, electromagnetic or optical signals that carry digital data streams. The processor system can transmit notifications and receive data, including program code, through the network(s), the network link and the communication interface.

While some exemplary shapes and sizes have been provided for elements of the medication adherence device 150, it should be understood to one of ordinary skill in the art that the unibody 150A, station 150B, and any other element described herein may be configured in a plurality of sizes and shapes including "T" shaped, "X" shaped, square shaped, rectangular shaped, cylinder shaped, cuboid shaped, hexagonal prism shaped, triangular prism shaped, or any other geometric or non-geometric shape, including combinations of shapes. It is not intended herein to mention all the possible alternatives, equivalent forms or ramifications of the invention. It is understood that the terms and proposed shapes used herein are merely descriptive, rather than limiting, and that various changes, such as to size and shape, may be made without departing from the spirit or scope of the invention.

Additionally, while some materials have been provided, in other embodiments, the elements that comprise the medication adherence device 150 may be made from or may comprise durable materials such as aluminum, steel, other metals and metal alloys, wood, hard rubbers, hard plastics, fiber reinforced plastics, carbon fiber, fiber glass, resins, polymers or any other suitable materials including combinations of materials. Additionally, one or more elements may be made from or comprise durable and slightly flexible materials such as soft plastics, silicone, soft rubbers, or any other suitable materials including combinations of materials. In some embodiments, one or more of the elements that comprise the device 150 may be coupled or connected together with heat bonding, chemical bonding, adhesives, clasp type fasteners, clip type fasteners, rivet type fasteners, threaded type fasteners, other types of fasteners, or any other suitable joining method. In other embodiments, one or more of the elements that comprise the device 150 may be coupled or removably connected by being press fit or snap fit together, by one or more fasteners such as hook and loop type or Velcro® fasteners, magnetic type fasteners, threaded type fasteners, sealable tongue and groove fasteners, snap fasteners, clip type fasteners, clasp type fasteners, ratchet type fasteners, a push-to-lock type connection method, a turn-to-lock type connection method, a slide-to-lock type connection method or any other suitable temporary connection method as one reasonably skilled in the art could envision to serve the same function. In further embodiments, one or more of the elements that comprise the device 150 may be coupled by being one of connected to and integrally formed with another element of the device 150.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A computer-implemented method for promoting medication adherence by a user of a client device based on the medication adherence history of the user, the method comprising the steps of:
    receiving treatment plan information for the user, wherein the treatment plan information comprises information describing a daily number of compliance events for a medication of the user;
    determining, via a computing device processor, if the user has missed a compliance event, using medication access information received from a medication adherence device, the medication adherence device comprising a housing configured to be removably coupled to a medicine container top and an access switch, the access switch generating medication access information when the housing is uncoupled from the medicine container top;
    identifying, via a computing device processor, a cumulative number of missed compliance events for the medication of the user; and
    producing, via a computing device processor, a blind spot on the display screen of the client device, wherein the blind spot obscures information on a portion of the display screen, and wherein the blind spot increases in size in proportion to an increasing cumulative number of missed compliance events.

2. The method of claim 1, wherein the medication adherence device comprises a processing unit and a network interface, and wherein the processing unit of the medication adherence device is configured to provide the medication access information to the client device of the user via the network interface of the medication adherence device.

3. The method of claim 1, wherein the medication adherence device comprises a processing unit and an inertial measurement unit, and wherein the inertial measurement provides medication access information describing movement of the device to the processing unit of the medication adherence device.

4. The method of claim 1, wherein the blind spot produced on the display screen is increased in size by approximately between one and five pixels for each missed compliance event.

5. The method of claim 1, wherein the blind spot produced on the display screen comprises a shape of a glaucoma associated scotoma.

6. The method of claim 5, wherein the blind spot produced on the display screen comprises a shape of a glaucoma associated scotoma selected from the group consisting essentially of: a nasal step type scotoma, a temporal wedge type scotoma, an superior arcuate defect type scotoma, a superior paracentral defect type scotoma, a fixation threatening paracentral defect type scotoma, a superior arcuate with peripheral breakthrough and early inferior defect type scotoma, a Bjerrum arcuate type scotoma, a tunnel vision defect with temporal crescent sparing type scotoma, and an end stage complete field loss type scotoma.

7. The method of claim 1, further comprising the step of providing, via a computing device processor, a reminder for each daily compliance event.

8. The method of claim 7, wherein the reminder is provided via the client device.

9. The method of claim 7, wherein the medication adherence device comprises a display, and wherein the reminder is a visual reminder generated by the display of the medication adherence device.

10. The method of claim 9, wherein the display is configured to visually display the medication access information.

* * * * *